US009028864B2

(12) United States Patent
Cipolla et al.

(10) Patent No.: US 9,028,864 B2
(45) Date of Patent: *May 12, 2015

(54) CONCENTRATED, INHALABLE ANTIBIOTIC FORMULATION

(75) Inventors: David C. Cipolla, San Ramon, CA (US); James Blanchard, El Granada, CA (US)

(73) Assignee: Aradigm Corporation, Hayward, CA (US)

(*) Notice: Subject to any disclaimer, the term of this patent is extended or adjusted under 35 U.S.C. 154(b) by 963 days.

This patent is subject to a terminal disclaimer.

(21) Appl. No.: 12/888,275

(22) Filed: Sep. 22, 2010

(65) Prior Publication Data

US 2011/0064796 A1 Mar. 17, 2011

Related U.S. Application Data

(63) Continuation of application No. 12/437,765, filed on May 8, 2009, now Pat. No. 8,119,156, which is a continuation-in-part of application No. 12/261,946, filed on Oct. 30, 2008, now Pat. No. 8,071,127, which is a continuation-in-part of application No. 11/876,539, filed on Oct. 22, 2007, now Pat. No. 8,268,347.

(60) Provisional application No. 60/862,753, filed on Oct. 24, 2006.

(51) Int. Cl.
| A61K 9/127 | (2006.01) |
| A61K 31/496 | (2006.01) |
| A61K 31/573 | (2006.01) |
| A61P 31/00 | (2006.01) |
| A61P 29/00 | (2006.01) |
| A61P 11/08 | (2006.01) |
| A61K 9/00 | (2006.01) |
| A61K 9/50 | (2006.01) |

(52) U.S. Cl.
CPC ............ *A61K 9/0043* (2013.01); *A61K 9/0078* (2013.01); *A61K 9/127* (2013.01); *A61K 9/5084* (2013.01)

(58) Field of Classification Search
CPC .... A61K 9/0078; A61K 9/0043; A61K 9/127
See application file for complete search history.

(56) References Cited

U.S. PATENT DOCUMENTS

| 5,006,343 A | 4/1991 | Benson et al. |
| 5,401,511 A | 3/1995 | Margalit |
| 5,823,178 A | 10/1998 | Lloyd et al. |
| 6,197,333 B1 | 3/2001 | Onyuksel et al. |
| 6,221,385 B1 | 4/2001 | Camu et al. |
| 6,316,024 B1 | 11/2001 | Allen et al. |
| 6,355,267 B1 | 3/2002 | Collins |
| 6,534,018 B1 | 3/2003 | Baker et al. |
| 6,623,671 B2 | 9/2003 | Coe et al. |
| 6,759,057 B1 | 7/2004 | Weiner et al. |
| 6,770,291 B2 | 8/2004 | Smyth-Templeton et al. |
| 6,855,296 B1 | 2/2005 | Baker et al. |
| 6,890,555 B1 | 5/2005 | Desai et al. |
| 8,119,156 B2 * | 2/2012 | Cipolla et al. ............... 424/450 |
| 8,268,347 B1 * | 9/2012 | Cipolla et al. ............... 424/450 |
| 8,414,915 B2 * | 4/2013 | Cipolla et al. ............... 424/450 |
| 2003/0224039 A1 | 12/2003 | Boni et al. |
| 2004/0009126 A1 | 1/2004 | Pilkiewicz et al. |
| 2004/0142026 A1 | 7/2004 | Boni et al. |
| 2005/0025822 A1 | 2/2005 | Wong et al. |
| 2006/0073198 A1 | 4/2006 | Boni et al. |
| 2007/0077290 A1 | 4/2007 | Li et al. |
| 2007/0196461 A1 | 8/2007 | Weers |
| 2009/0274754 A1 | 11/2009 | Cipolla et al. |
| 2011/0064796 A1 | 3/2011 | Cipolla et al. |
| 2011/0150983 A1 * | 6/2011 | Cipolla et al. ............... 424/450 |

FOREIGN PATENT DOCUMENTS

| CA | 2101241 | 7/1993 |
| CA | 2215716 | 9/1997 |
| CA | 2174803 | 10/1997 |
| CN | 1747738 | 3/2006 |
| DE | EP1083886 | * 4/2003 ............... A61K 9/20 |
| EP | 0 652 008 | 5/1995 |
| EP | 1083881 | 3/2001 |
| EP | 1 190 705 | 3/2002 |
| EP | 1083886 | 4/2003 |
| EP | 0 825 852 | 7/2004 |
| WO | 99/51202 | 10/1999 |
| WO | 01/00173 | 1/2001 |
| WO | 01/15678 | 3/2001 |
| WO | 2004/110346 | 12/2004 |
| WO | 2004/110493 | 12/2004 |
| WO | 2010/111641 | 9/2010 |
| WO | 2011/050206 | 4/2011 |
| WO | 2012/050945 | 4/2012 |

OTHER PUBLICATIONS

Majumdar et al (Antimicrob. Agents Chemother. 1992, 36(12):2808-2815).*
Maurer et al (Biopchimica et Biophysica Acta. 1998, 1374:9-20).*
Kyriacos et al. (Journal of Food and Drug Analysis. 2009; 17(2): 78-84).*
Bangham et al., "Diffusion of Univalent Ions across the Lamellae of Swollen Phospholipids" J. Mol. Biol., 13:238-252 (1965).
Conley et al., "Aerosol Delivery of Liposome-Encapsulated Ciprofloxacin: Aerosol Characterization and Efficacy against *Francisella tularensis* Infection in Mice" Antimicrobial Angents, 41(6):1288-1292 (Jun. 1997).
Desai et al., "A Novel Approach to the Pulmonary Delivery of Liposomes in Dry Powder Form to Eliminate the Deleterious Effects of Milling" Journal of Pharmaceutical Sciences, 91(2):482-491 (Feb. 2002).
Desai et al., "A facile method of delivery of liposomes by nebulization" Journal of Controlled Release, 84:69-78 (2002).
Wong et al., "Liposome delivery of ciprofloxacin against intracellular *Francisella tularensis* infection" Journal of Controlled Release, 92:265-273 (2003).

(Continued)

*Primary Examiner* — Scott Long
(74) *Attorney, Agent, or Firm* — Karl Bozicevic; Bozicevic, Field & Francis LLP

(57) ABSTRACT

A concentrated inhalable formulation of an antibiotic drug such as ciprofloxacin is disclosed. The antibiotic is formulated with sodium acetate and liposome which incorporate antibiotic. The formulation is aerosolized and inhaled for treatment of respiratory tract infections and other medical conditions.

1 Claim, 3 Drawing Sheets

(56) References Cited

OTHER PUBLICATIONS

Lipuma JJ., Microbiological and immunologic considerations with aerosolized drug delivery. Chest. Sep. 2001;120(3 Suppl):118S-123S.

Moss RB., Administration of aerosolized antibiotics in cystic fibrosis patients. Chest. Sep. 2001;120(3 Suppl):107S-113S.

Smith AL, et al. Safety of aerosol tobramycin administration for 3 months to patients with cystic fibrosis. Ped Pulmonol. 1989:7(4):265-271.

Van Heeckeren AM, et al. Role of Cftr genotype in the response to chronic *Pseudomonas aeruginosa* lung infection in mice. Am J Physiol Lung Cell Mol Physiol. Nov. 2004;287(5):L944-52. Epub Jul. 9, 2004.

Van Heeckeren AM, et al.. Delivery of CFTR by adenoviral vector to cystic fibrosis mouse lung in a model of chronic *Pseudomonas aeruginosa* lung infection. Am J Physiol Lung Cell Mol Physiol. Apr. 2004;286(4):L717-26. Epub Sep. 26, 2003.

Van Heeckeren A, et al.., Effects of bronchopulmonary inflammation induced by *Pseudomonas aeruginosa* on adenovirus-mediated gene transfer to airway epithelial cells in mice. Gene Ther. Mar. 1998;5(3):345-51.

Van Heeckeren AM, et al., Murine models of chronic *Pseudomonas aeruginosa* lung infection. Lab Anim. Jul. 2002;36(3):291-312.

Van Heeckeren AM, et al., Effect of *Pseudomonas* infection on weight loss, lung mechanics, and cytokines in mice. Am J Respir Crit Care Med. Jan. 2000;161(1):271.

Weber A, et al., Nebulizer delivery of tobramycin to the lower respiratory tract. Pediatr Pulmonol. May 1994;17 (5):331-9.

Elhissi et al., "Formulations generated from ethanol-based proliposomes for delivery via medical nebulizers" Journal of Pharmacy and Pharmacology, Jul. 2006, 58:887-894.

Anacona et al., "Synthesis and antibacterial activity of metal complexes of ciprofloxacin" Transition Metal Chemistry (2001) 26:228-231.

* cited by examiner

CONCENTRATED, INHALABLE ANTIBIOTIC FORMULATION

CROSS-REFERENCE

This application is a continuation of U.S. patent application Ser. No. 12/437,865 filed May 8, 2009 which is a continuation-in-part application of U.S. patent application Ser. No. 12/261,946, filed Oct. 30, 2008 (currently pending), which is a continuation-in-part of application of U.S. patent application Ser. No. 11/876,539 filed Oct. 22, 2007 (currently pending), which claims the benefit of priority to U.S. Provisional Patent Application Ser. No. 60/862,753 filed Oct. 24, 2006, all of which are incorporated herein by reference in their entirety noting that the current application controls to the extent there is any contradiction with any earlier application and to which applications we claim priority under 35 USC §120.

FIELD OF THE INVENTION

The present invention relates to pharmaceutical compositions for inhalation such as for treating respiratory tract infections caused by a variety of microorganisms. In particular, the present invention relates to a highly concentrated, inhalable antibiotic formulation.

BACKGROUND OF THE INVENTION

Respiratory tract infections are caused by a variety of microorganisms. Infections which are persistent have a myriad of consequences for the health care community including increased treatment burden and cost, and for the patient in terms of more invasive treatment paradigms and potential for serious illness or even death. It would be beneficial if an improved treatment paradigm were available to provide prophylactic treatment to prevent susceptible patients from acquiring respiratory tract infections as well as increasing the rate or effectiveness of eradicating the infections in patients already infected with the microorganisms.

In particular, cystic fibrosis (CF) is one example of a disease in which patients often acquire persistent or tenacious respiratory tract infections. CF is a life-threatening genetic disease affecting approximately 30,000 people in the United States with a frequency of approximately one in every 2,500 live births (Fitzsimmons S C, 1993). The name cystic fibrosis refers to the characteristic scarring (fibrosis) and cyst formation within the pancreas, first recognized in the 1930s. About 1,000 new cases of CF are diagnosed each year. More than 80 percent of patients are diagnosed by age three; however, nearly 10 percent of newly diagnosed cases are age 18 or older.

The primary CF defect is expressed as altered ion transport via the cystic fibrosis transmembrane conductance regulator (CFTR), which is the protein regulating cyclic-AMP-mediated chloride conductance at the apical membranes of secretory epithelia (Schroeder S A et al., 1995). Specifically, the normal release of intracellular chloride into extracellular fluids fails to respond to normal cAMP elevation. This impaired release of chloride results in the dehydration of surrounding respiratory and intestinal mucosal linings and impaired sodium reabsorption of the sudoriferous glands. This mucosal dehydration, coupled with inflammatory and infective by-products, creates a thick and tenacious mucus that clogs and damages airways. Prompt, aggressive treatment of CF symptoms can extend the lives of those with the disease.

Although most people without CF have two working copies of the CFTR gene, only one is needed to prevent cystic fibrosis. CF develops when neither gene works normally. Therefore, CF is considered an autosomal recessive disease. There are more than 1,500 different genetic mutations associated with the disease (CFTR mutation database, 2006), thus making homozygous and heterozygous screening procedures difficult (Zielenski J et al., 1995). However, approximately two thirds of the mutations are found to be delta F508, making it the most common CF mutation (CF Genetic Analysis Consortium, 1994).

The ongoing treatment of CF depends upon the stage of the disease and the organs involved. Clearing mucus from the lungs is an important part of the daily CF treatment regimen. Chest physical therapy is one form of airway clearance, and it requires vigorous percussion (by using cupped hands) on the back and chest to dislodge the thick mucus from the lungs. Other forms of airway clearance can be done with the help of mechanical devices used to stimulate mucus clearance. Other types of treatments include: Pulmozyme®, an inhaled mucolytic agent shown to reduce the number of lung infections and improve lung function (Hodson M, 1995); TOBI® (tobramycin solution for inhalation), an aerosolized aminoglycoside antibiotic used to treat lung infections and also shown to improve lung function (Weber A et al., 1994); and oral azithromycin, a macrolide antibiotic shown to reduce the number of respiratory exacerbations and the rate of decline of lung function (Wolter J et al., 2002).

As discussed above, high rates of colonization and the challenge of managing *Pseudomonas aeruginosa* infections in patients with cystic fibrosis (CF) have necessitated a search for safe and effective antibiotics. Currently, therapy with an aminoglycoside in combination with a beta-lactam or a quinolone antibiotic is the standard. A 96-week series of clinical studies including 520 patients with moderate-to-severe CF showed that patients receiving inhaled tobramycin spent 25 to 33% fewer days in the hospital and experienced significant increases in lung function (Moss R B, 2001). These results demonstrate the effectiveness of inhaled antibiotics to treat CF. However, the development of drug resistant strains, especially *P. aeruginosa*, is a major concern with the long-term delivery of aerosolized antibiotics via inhalation (LiPuma J J, 2001).

While azithromycin possesses activity against *Staphylococcus aureus, Haemophilus influenzae*, and *Streptococcus pneumoniae*, it has no direct activity against *Pseudomonas aeruginosa, Burkholderia cepacia*, or other gram-negative non-fermenters (Lode H et al., 1996). Tobramycin possesses activity against *P. aeruginosa*; however, the increase in the number of patients with resistant isolates on continuous therapy from ~10% to 80% after 3 months (Smith A L et al., 1989) has led to the intermittent dosing regimen of 28-days-on followed by 28-days-off therapy. Even on intermittent inhaled tobramycin therapy, the percentage of patients with multiresistant *P. aeruginosa* increased from 14% at baseline to 23% after 18 months of treatment (LiPuma J J, 2001). The development of a therapeutic regimen that delivers the anti-infective therapy in a continuous fashion, while still inhibiting the emergence of resistant isolates, may provide an improved treatment paradigm. It is noteworthy that chronic *P. aeruginosa* airway infections remain the primary cause of morbidity and mortality in CF patients. When patients experience pulmonary exacerbations, the use of antipseudomonal therapy, frequently consisting of a β-lactam and an aminoglycoside, may result in clinical improvement and a decrease in bacterial burden. Eradication of the infection, however, is quite rare.

In CF airways, *P. aeruginosa* initially has a non-mucoid phenotype, but ultimately produces mucoid exopolysaccharide and organizes into a biofilm, which indicates the airway infection has progressed from acute to chronic. Bacteria in biofilms are very slow growing due to an anaerobic environment and are inherently resistant to antimicrobial agents, since sessile cells are much less susceptible than cells growing planktonically. It has been reported that biofilm cells are at least 500 times more resistant to antibacterial agents (Costerton J W et al., 1995). Thus, the transition to the mucoid phenotype and production of a biofilm contribute to the persistence of *P. aeruginosa* in CF patients with chronic infection by protecting the bacteria from host defenses and interfering with the delivery of antibiotics to the bacterial cell.

Although much effort has been made to improve the care and treatment of individuals with CF, and the average lifespan has increased, the median age of survival for people with CF is only to the late 30 s (CF Foundation web site, 2006). Thus, a continuing need exists for improved formulations of anti-infectives, especially for administration by inhalation. The present invention addresses this need.

Ciprofloxacin is a fluoroquinolone antibiotic that is indicated for the treatment of lower respiratory tract infections due to *P. aeruginosa*, which is common in patients with cystic fibrosis. Ciprofloxacin is broad spectrum and, in addition to *P. aeruginosa*, is active against several other types of gram-negative and gram-positive bacteria. It acts by inhibition of topoisomerase II (DNA gyrase) and topoisomerase IV, which are enzymes required for bacterial replication, transcription, repair, and recombination. This mechanism of action is different from that for penicillins, cephalosporins, aminoglycosides, macrolides, and tetracyclines, and therefore bacteria resistant to these classes of drugs may be susceptible to ciprofloxacin. Thus, CF patients who have developed resistance to the aminoglycoside tobramycin (TOBI), can likely still be treated with ciprofloxacin. There is no known cross-resistance between ciprofloxacin and other classes of antimicrobials.

Despite its attractive antimicrobial properties, ciprofloxacin does produce bothersome side effects, such as GI intolerance (vomiting, diarrhea, abdominal discomfort), as well as dizziness, insomnia, irritability and increased levels of anxiety. There is a clear need for improved treatment regimes that can be used chronically, without resulting in these debilitating side effects.

Delivering ciprofloxacin as an inhaled aerosol has the potential to address these concerns by compartmentalizing the delivery and action of the drug in the respiratory tract, which is the primary site of infection.

Currently there is no aerosolized form of ciprofloxacin with regulatory approval for human use, capable of targeting antibiotic delivery direct to the area of primary infection. In part this is because the poor solubility and bitterness of the drug have inhibited development of a formulation suitable for inhalation. Furthermore, the tissue distribution of ciprofloxacin is so rapid that the drug residence time in the lung is too short to provide additional therapeutic benefit over drug administered by oral or IV routes.

Phospholipid vehicles as drug delivery systems were rediscovered as "liposomes" in 1965 (Bangham et al., 1965). The therapeutic properties of many active pharmaceutical ingredients (APIs) can be improved by incorporation into liposomal drug delivery systems. The general term liposome covers a wide variety of structures, but generally all are composed of one or more lipid bilayers enclosing an aqueous space in which drugs can be encapsulated. The liposomes applied in this program are known in the drug delivery field as large unilamellar vesicles (LUV), which are the preferred liposomal structures for IV drug administration.

Liposome encapsulation improves biopharmaceutical characteristics through a number of mechanisms including altered drug pharmacokinetics and biodistribution, sustained drug release from the carrier, enhanced delivery to disease sites, and protection of the active drug species from degradation. Liposome formulations of the anticancer agents doxorubicin (Myocet®/Evacet®, Doxyl®/Caelyx®), daunorubicin (DaunoXome®) the anti-fungal agent amphotericin B (Abelcet®, AmBisome®, Amphotec®) and a benzoporphyrin (Visudyne®) are examples of successful products introduced into the US, European and Japanese markets over the last decade. Furthermore, a number of second-generation products have been in late-stage clinical trials, including Inex's vincristine sulphate liposomes injection (VSLI). The proven safety and efficacy of lipid-based carriers make them attractive candidates for the formulation of pharmaceuticals.

Therefore, in comparison to the current ciprofloxacin formulations, a liposomal ciprofloxacin aerosol formulation should offer several benefits: 1) higher drug concentrations, 2) increased drug residence time via sustained release at the site of infection, 3) decreased side effects, 4) increased palatability, 5) better penetration into the bacteria, and 6) better penetration into the cells infected by bacteria. It has previously been shown that inhalation of liposome-encapsulated fluoroquinolone antibiotics may be effective in treatment of lung infections. In a mouse model of *F. tularensis* liposomal encapsulated fluoroquinolone antibiotics were shown to be superior to the free or unencapsulated fluoroquinolone by increasing survival (CA2,215,716, CA2,174,803, and CA2,101,241).

Another application, EP1083881B1, describes liposomes containing a drug-conjugate comprising a quinolone compound covalently attached to an amino acid. Yet another application, U.S. Publication No. 20004142026, also describes the use of liposome-encapsulated antibiotics and the potential for administration of a lower dose of a liposome-encapsulated anti-infective, by a factor of 10 or 100, than for the free unencapsulated anti-infective.

It has also been reported that the presence of sub-inhibitory concentrations of antibiotic agents within the depths of the biofilm will provide selective pressures for the development of more resistant phenotypes (Gilbert P et al., 1997). This may be partly due to the failure of the antibiotics to penetrate the glycocalyx adequately.

SUMMARY OF THE INVENTION

An aspect of the invention is an aerosolized, bi-phasic, formulation which is aerosolized to create a bi-phasic aerosol of inhaled droplets or particles. The droplets or particles comprise a free drug (e.g., an anti-infective compound) in which drug is not encapsulated and which may be ciprofloxacin. The particles further comprise a liposome which encapsulates a drug such as an anti-infective compound which also may be ciprofloxin. The free and liposome encapsulated drug are included within a pharmaceutically acceptable excipient which is formulated for aerosolized delivery. The particles may further include an additional therapeutic agent which may be free and/or in a liposome and which can be any pharmaceutically active drug which is different from the first drug.

The formulation and the resulting particles created when the formulation is aerosolized are comprised of a pharmaceutically acceptable carrier, free drug, and drug encapsulated within liposomes. In some situations the pharmaceutically acceptable carrier can be completely eliminated such as when the free drug is in a liquid state. However, the carrier is generally necessary to provide a solvent for the free drug and that solvent may be water, ethanol, a combination of water and ethanol or other useful solvents. The percentage of solvent in the formulation may vary from 0% to 90% but is generally kept at a level which is sufficiently high to maintain the drug in solution at the pH of the formulation. That level will vary from drug to drug and vary as the pH varies. The carrier can be present in the formulation in an amount of 10%, 20%, 30%, 40%, 50%, 60% etc. or more or any incremental amounts there in between.

The formulation includes the drug in two different forms. First, the drug is in a free form which is either liquid or dissolved in a solvent. Second, the drug is encapsulated in liposomes. The ratio of the free drug to the drug encapsulated in liposomes can vary. Generally, the free drug makes up 5%, 10%, 20%, 30%, etc. up to 80% of the formulation. The drug present within the liposome makes up the remaining percentage of drug present in the formulation. Thus, drug present in the liposomes can be present in the amount of from 20% up to 95% of the total drug present in the formulation.

The formulation may have a pH of 7.4±20%. In some aspects of the invention the formulation is prepared at a relatively low pH such as 5.4 and allowed to adjust to a pH of about 7.4 after it is delivered. Alternatively, the formulation can be formulated at a high pH of about 9.4 and allowed to adjust downward to 7.4 after administration.

The formulation includes liposomes which have the encapsulated pharmaceutically active drug therein which liposomes are designed to provide for controlled release of the drug. Controlled release of this aspect in the invention indicates that the drug may be released in an amount of about 0.1% to 100% per hour over a period of time of 1-24 hours or 0.5% to 20% per hour over a period of time of 1-12 hours, or alternatively, releases about 2% to 10% per hour over a period of time of about 1 to 6 hours. Incremental amounts in terms of the percentage of the drug and the number of hours which are between the ranges provided above in half percentage amounts and half hour amounts and other incremental amounts are intended to be encompassed by the present invention.

One aspect of the invention is a formulation comprising liposomes which are delivered via an aerosol to the lungs of a human patient, the liposomes comprising free and encapsulated ciprofloxacin or other anti-infective agent. The liposomes may be unilamellar or multilamellar, and may be bioadhesive, containing a molecule such as hyaluronic acid. At least one therapeutic agent in addition to the free and liposome-encapsulated anti-infective may also be included in the composition. That therapeutic agent may be free drug or encapsulated drug present with a pharmaceutically acceptable carrier useful for direct inhalation into human lungs. The other drugs may include enzymes to reduce the viscoelasticity of the mucus such as DNase or other mucolytic agents, chemicals to upregulate the chloride ion channel or increase flow of ions across the cells, including lantibiotics such as duramycin, agents to promote hydration or mucociliary clearance including epithelial sodium channel (ENaC) inhibitors or P2Y2 agonists such as denufosol, elastase inhibitors including Alpha-1 antitrypsin (AAT), bronchodilators, steroids, N-acetylcysteine, interferon gamma, interferon alpha, agents that enhance the activity of the antibiotic against biofilm bacteria such as sodium salicylate (Polonio R E et al., 2001), or antibiotics known to those skilled in the art. Inflammation and constriction of the airways are also associated with cystic fibrosis and its treatment. Accordingly, bronchodilators, such as $\beta_2$-adrenergic receptor agonists and antimuscarinics, and anti-inflammatory agents, including inhaled corticosteroids, non-steroidal anti-inflammatories, leukotriene receptor antagonists or synthesis inhibitors, and others, may also be combined with an anti-infective.

A further aspect of the invention is a method for treating cystic fibrosis in a patient, the method comprising administering a formulation comprising the anti-infective; e.g., ciprofloxacin, encapsulated in liposomes to the patient. The formulation is preferably administered by inhalation to the patient.

According to another aspect of the present invention, a formulation comprising both a free and encapsulated anti-infective provides an initially high therapeutic level of the anti-infective in the lungs to overcome the barrier to eradicate the difficult to treat biofilm bacteria, while maintaining a sustained release of anti-infective over time. While some aspects of biofilm resistance are poorly understood, the dominant mechanisms are thought to be related to: (i) modified nutrient environments and suppression of growth rate within the biofilm; (ii) direct interactions between the exopolymer matrices, and their constituents, and antimicrobials, affecting diffusion and availability; and (iii) the development of biofilm/attachment-specific phenotypes (Gilbert P et al., 1997). The intent of the immediate-release anti-infective; e.g., ciprofloxacin, is thus to rapidly increase the antibiotic concentration in the lung to therapeutic levels around the difficult to eradicate biofilm bacteria to address the challenges of lower diffusion rate of antibiotic to and within the biofilm. The sustained-release anti-infective; e.g., ciprofloxacin, serves to maintain a therapeutic level of antibiotic in the lung thereby providing continued therapy over a longer time frame, increasing efficacy, reducing the frequency of administration, and reducing the potential for resistant colonies to form. The high levels of free antibiotic may also serve to attenuate the cytotoxic response to the presence of liposomes (i.e., particles) in the lung and thus reduce the influx of activated macrophages.

According to another aspect of the present invention, the immediate release of high levels of an anti-infective may allow enhanced penetration of the glycocalyx. The sustained release of the anti-infective may ensure that the anti-infective agent never falls below the sub-inhibitory concentration and so reduces the likelihood of forming resistance to the anti-infective.

Although ciprofloxacin is a particularly useful anti-infective in this invention, there is no desire to limit this invention to ciprofloxacin. Other antibiotics or anti-infectives can be used such as those selected from the group consisting of: an aminoglycoside, a tetracycline, a sulfonamide, p-aminobenzoic acid, a diaminopyrimidine, a quinolone, a.beta.-lactam, a.beta.-lactam and a.beta.-lactamase inhibitor, chloraphenicol, a macrolide, penicillins, cephalosporins, corticosteroid, prostaglandin, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, terbinafine, or any combination thereof.

These and other objects, advantages, and features of the invention will become apparent to those persons skilled in the art upon reading the details of the formulations and methodology as more fully described below.

BRIEF DESCRIPTION OF THE DRAWINGS

Aspects and embodiments of the invention are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
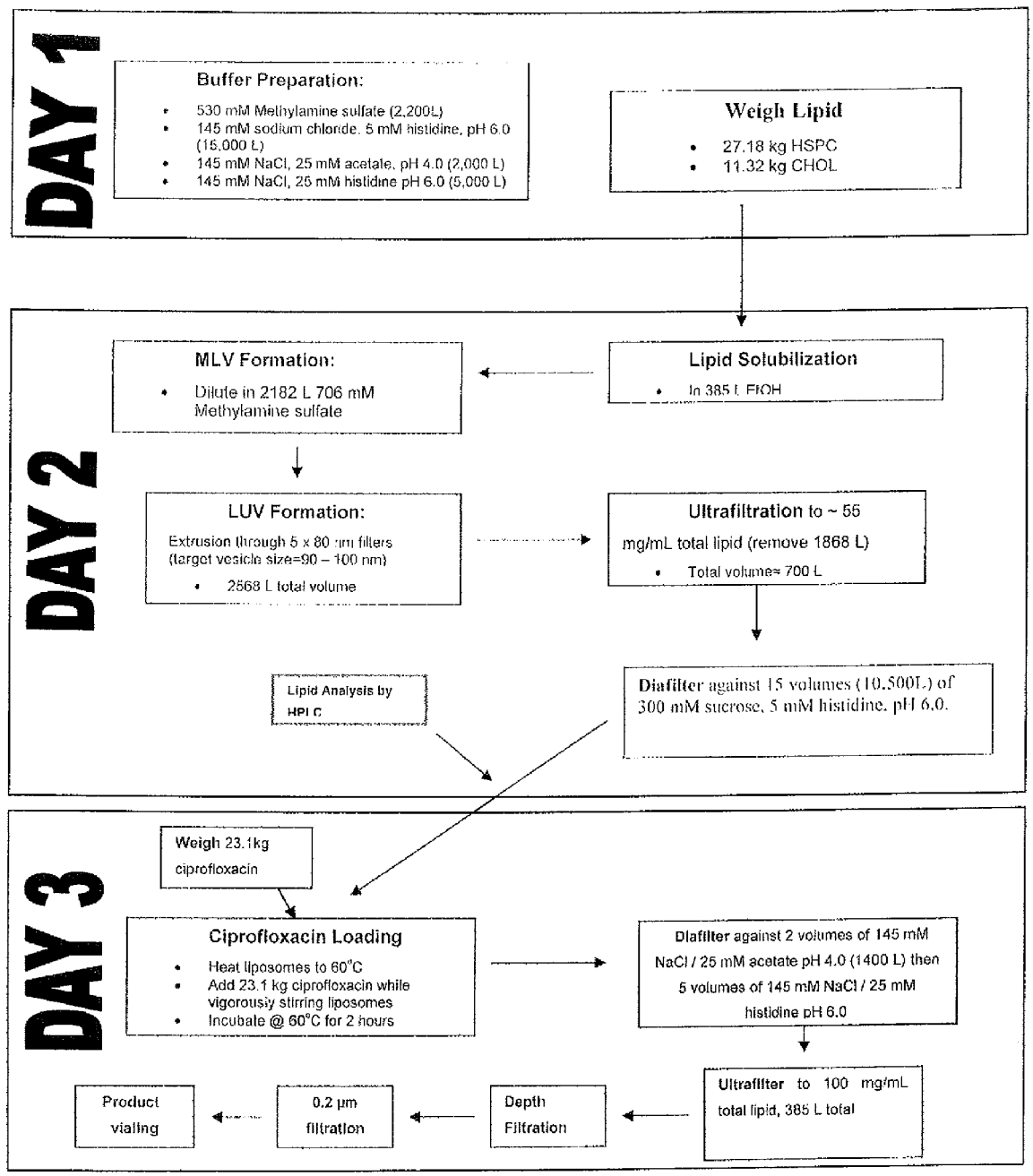
FIG. 1 is a manufacturing flow chart of liposomal ciprofloxacin for inhalation (HSPC/Chol –10 L Batch).

Before the present method of formulating ciprofloxacin-encapsulated liposomes and delivery of such for prevention and/or treatment of cystic fibrosis and other medical conditions, and devices and formulations used in connection with such are described, it is to be understood that this invention is not limited to the particular methodology, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, anti-infective refers to agents that act against infections, such as bacterial, viral, fungal, mycobacterial, or protozoal infections.

Anti-infectives covered by the invention include but are not limited to quinolones (such as nalidixic acid, cinoxacin, ciprofloxacin and norfloxacin and the like), sulfonamides (e.g., sulfanilamide, sulfadiazine, sulfamethaoxazole, sulfisoxazole, sulfacetamide, and the like), aminoglycosides (e.g., streptomycin, gentamicin, tobramycin, amikacin, netilmicin, kanamycin, and the like), tetracyclines (such as chlortetracycline, oxytetracycline, methacycline, doxycycline, minocycline and the like), para-aminobenzoic acid, diaminopyrimidines (such as trimethoprim, often used in conjunction with sulfamethoxazole, pyrazinamide, and the like), penicillins (such as penicillin G, penicillin V, ampicillin, amoxicillin, bacampicillin, carbenicillin, carbenicillin indanyl, ticarcillin, azlocillin, mezlocillin, piperacillin, and the like), penicillinase resistant penicillin (such as methicillin, oxacillin, cloxacillin, dicloxacillin, nafcillin and the like), first generation cephalosporins (such as cefadroxil, cephalexin, cephradine, cephalothin, cephapirin, cefazolin, and the like), second generation cephalosporins (such as cefaclor, cefamandole, cefonicid, cefoxitin, cefotetan, cefuroxime, cefuroxime axetil, cefinetazole, cefprozil, loracarbef, cefo-ranide, and the like), third generation cephalosporins (such as cefepime, cefoperazone, cefotaxime, ceftizoxime, ceftriaxone, ceftazidime, cefixime, cefpodoxime, ceftibuten, and the like), other beta-lactams (such as imipenem, meropenem, aztreonam, clavulanic acid, sulbactam, tazobactam, and the like), beta-lactamase inhibitors (such as clavulanic acid), chloramphenicol, macrolides (such as erythromycin, azithromycin, clarithromycin, and the like), lincomycin, clindamycin, spectinomycin, polymyxin B, polymixins (such as polymyxin A, B, C, D, E.sub.1(colistin A), or E.sub.2, colistin B or C, and the like) colistin, vancomycin, bacitracin, isoniazid, rifampin, ethambutol, ethionamide, aminosalicylic acid, cycloserine, capreomycin, sulfones (such as dapsone, sulfoxone sodium, and the like), clofazimine, thalidomide, or any other antibacterial agent that can be lipid encapsulated. Anti-infectives can include antifungal agents, including polyene antifungals (such as amphotericin B, nystatin, natamycin, and the like), flucytosine, imidazoles (such as miconazole, clotrimazole, econazole, ketoconazole, and the like), triazoles (such as itraconazole, fluconazole, and the like), griseofulvin, terconazole, butoconazole ciclopirax, ciclopirox olamine, haloprogin, tolnaftate, naftifine, terbinafine, or any other antifungal that can be lipid encapsulated or complexed and pharmaceutically acceptable salts thereof and combinations thereof. Discussion and the examples are directed primarily toward ciprofloxacin but the scope of the application is not intended to be limited to this anti-infective. Combinations of drugs can be used.

Bronchodilators covered by the invention include but are not limited to $\beta_2$-adrenergic receptor agonists (such as albuterol, bambuterol, salbutamol, salmeterol, formoterol, arformoterol, levosalbutamol, procaterol, indacaterol, carmoterol, milveterol, procaterol, terbutaline, and the like), and antimuscarinics (such as trospium, ipratropium, glycopyrronium, aclidinium, and the like). Combinations of drugs may be used.

Anti-inflammatories covered by the invention include but are not limited to inhaled corticosteroids (such as beclometasone, budesonide, ciclesonide, fluticasone, etiprednol, mometasone, and the like), leukotriene receptor antagonists and leukotriene synthesis inhibitors (such as montelukast, zileuton, ibudilast, zafirlukast, pranlukast, amelubant, tipelukast, and the like), cyclooxygenase inhibitors (such as ibuprofen, ketoprofen, ketorolac, indometacin, naproxen, zaltoprofen, lornoxicam, meloxicam, celecoxib, lumiracoxib, etoricoxib, piroxicam, ampiroxicam, cinnoxicam, diclofenac, felbinac, lornoxicam, mesalazine, triflusal, tinoridine, iguratimod, pamicogrel, and the like). Combinations of drugs may be used.

As used herein, "Formulation" refers to the liposome-encapsulated anti-infective, with any excipients or additional active ingredients, either as a dry powder or suspended or dissolved in a liquid.

The terms "subject," "individual," "patient," and "host" are used interchangeably herein and refer to any vertebrate, particularly any mammal and most particularly including human subjects, farm animals, and mammalian pets. The subject may be, but is not necessarily under the care of a health care professional such as a doctor.

A "stable" formulation is one in which the protein or enzyme therein essentially retains its physical and chemical stability and integrity upon storage and exposure to relatively high temperatures. Various analytical techniques for measuring peptide stability are available in the art and are reviewed in Peptide and Protein Drug Delivery, 247-301, Vincent Lee Ed., Marcel Dekker, Inc., New York, N.Y., Pubs. (1991), and Jones, A. (1993) *Adv. Drug Delivery Rev.* 10:29-90. Stability can be measured at a selected temperature for a selected time period.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the claimed methods and compositions.

Invention In General

Ciprofloxacin is a well-established and extensively utilized broad-spectrum fluoroquinolone antibiotic that is indicated for the treatment of lower respiratory tract infections due to *P. aeruginosa*, which is common in patients with cystic fibrosis. The primary advantage of inhaled antimicrobials is that they target antibiotic delivery to the area of primary infection and bypass GI-related side effects; however, the poor solubility and bitterness of the drug have limited development of a formulation suitable for inhalation. Furthermore, the rapid tissue distribution of ciprofloxacin means a short drug residence time in the lung thus limiting therapeutic benefit over oral or IV drug administration. A liposome-encapsulated formulation of ciprofloxacin decreases the limitations and improves management of pulmonary infections due to *P. aeruginosa* pulmonary infections in patients with CF through improved biopharmaceutical characteristics and mechanisms such as altered drug PK and biodistribution, sustained drug release from the carrier, enhanced delivery to disease sites, and protection of the active drug species from degradation.

Preclinical studies demonstrate the efficacy of liposomal ciprofloxacin in a biofilm inhibitory concentration assay using clinical isolates of *Pseudomonas aeruginosa*, a CF mouse model of *P. aeruginosa* lung infection and in a mouse model of *Francisella tularensis* lung infection. Safety pharmacology studies of respiration in rats and dogs of inhaled liposomal ciprofloxacin found no marked effects upon respiratory parameters. These studies showed that the inhalation of levels of "free" ciprofloxacin together with the liposomal ciprofloxacin formulation allowed the dosing of greater amounts of liposomal ciprofloxacin without observation of focal macrophage accumulation or increases in the proinflammatory cytokine IL-1β in the lung fluid. This finding is more generally applicable to other liposomal formulations delivered to the lung. These results are also applicable to pharmaceutical preparations or formulations which otherwise may result in increases in macrophage accumulation in the lung or the increase in proinflammatory cytokines in the lung in response to the therapy.

The invention includes a formulation that combines ciprofloxacin (or a different immune blunting agent; e.g., zithromax) with another drug; e.g., liposomal ciprofloxacin, delivered via the inhalation route. The liposomal encapsulated ciprofloxacin may be substituted with an antibiotic other than ciprofloxacin and may be formulated without using liposomes. The other drug does not have to be an antibiotic and may be any drug that is believed to have some beneficial properties when delivered to the lung.

The invention is not limited to the treatment of CF patients. In fact, there are many patients and indications for which this therapy may be beneficial, including bronchiectasis, pneumonia, and other lung infections. This treatment paradigm would also apply to other lung diseases including COPD, asthma, pulmonary hypertension and others in which a formulation of free ciprofloxacin is delivered in combination with another drug to allow higher dosing of the other drug or safer administration of the other drug.

The invention also relates to the use of inhaled free ciprofloxacin (or a different immune blunting agent; e.g., zithromax) in combination with other drugs given via inhalation. These other drugs may include a nucleotide sequence which may be incorporated into a suitable delivery vector such as a plasmid or viral vector. The other drug may be a therapeutic nucleotide sequence (DNA, RNA, siRNA), enzymes to reduce the viscoelasticity of the mucus such as DNase and other mucolytic agents, chemicals to upregulate the chloride ion channel or increase flow of ions across the cells, nicotine, P2Y2 agonists, elastase inhibitors including Alpha-1 antitrypsin (AAT), N-acetylcysteine, antibiotics and cationic peptides, such as lantibiotics, and specifically duramycin, short-acting bronchodilators (e.g., β2-adrenergic receptor agonists like albuterol or indacaterol), M3 muscarinic antagonists (e.g., ipatropium bromide), K+-channel openers, long-acting bronchodilators (e.g., formoterol, salmeterol), steroids (e.g., budesonide, fluticasone, triamcinolone, beclomethasone, ciclesonide, etc.), xanthines, leukotriene antagonists (e.g., montelukast sodium), phosphodiesterase 4 inhibitors, adenosine receptor antagonists, other miscellaneous anti-inflammatories (e.g., Syk kinase inhibitors (AVE-0950), tryptase inhibitors (AVE-8923 & AVE-5638), tachykinin antagonists (AVE-5883), inducible nitric oxide synthase inhibitors (GW-274150) and others), transcription factor decoys, TLR-9 agonists, antisense oligonucleotides, siRNA, DNA, CGRP, lidocaine, inverse β2-agonists, anti-infective oxidative therapies, cytokine modulators (e.g., CCR3 receptor antagonists (GSK-766994, DPC-168, AZD-3778), TNF-α production inhibitors (LMP-160 & YS-TH2), and IL-4 antagonists (AVE-0309)), small molecule inhibitors of IgE, cell adhesion molecule (CAM) inhibitors, small molecules targeting the VLA4 receptor or integrin α4β1 (e.g., R-411, PS-460644, DW-908e, & CDP-323), immunomodulators including those that block T-cell signaling by inhibition of calcineurin (Tacrolimus), heparin neutralizers (Talactoferrin alfa), cytosolic PLA2 inhibitors (Efipladib), or combinations thereof. The delivery of the combination products may be achieved by combining the drugs into one stable formulation, or providing the drugs in separate containers to be combined at the time of administration or alternatively by sequentially delivering the products.

I. Generation of Liposomes Containing Ciprofloxacin

According to aspects of the instant invention, a method is provided for formulating ciprofloxacin and other anti-infectives by encapsulating these drugs in liposomes. Composed of naturally-occurring materials which are biocompatible and biodegradable, liposomes are used to encapsulate biologically active materials for a variety of purposes. Having a variety of layers, sizes, surface charges and compositions, numerous procedures for liposomal preparation and for drug encapsulation within them have been developed, some of which have been scaled up to industrial levels. Liposomes can be designed to act as sustained release drug depots and, in certain applications, aid drug access across cell membranes.

The sustained release property of the liposomes may be regulated by the nature of the lipid membrane and by the inclusion of other excipients in the composition of the liposomes. Extensive research in liposome technology over many years has yielded a reasonable prediction of the rate of drug release based on the composition of the liposome formulation. The rate of drug release is primarily dependent on the nature of the phospholipids, e.g. hydrogenated (—H) or unhydrogenated (—G), or the phospholipid/cholesterol ratio (the higher this ratio, the faster the rate of release), the hydrophilic/lipophilic properties of the active ingredients and by the method of liposome manufacturing.

Methods for making bioadhesive liposomes can be found, for example, in U.S. Pat. No. 5,401,511 which is incorporated herein by reference in its entirety along with the patents and publications cited therein which describe liposomes and methods of making liposomes. In recent years, successful attempts have been made to bind different substances to liposomes. For example, binding of chymotrypsin to liposomes has been studied as a model for binding substances to liposomal surfaces. Recognizing substances, including antibodies, glycoproteins and lectins, have been bound to liposomal surfaces in an attempt to confer target specificity to the liposomes.

The number and surface density of the discrete sites on the liposomal surfaces for covalent bonding are dictated by the liposome formulation and the liposome type. The liposomal surfaces also have sites for noncovalent association. Covalent binding is preferred as noncovalent binding might result in dissociation of the recognizing substances from the liposomes at the site of administration since the liposomes and the bioadhesive counterparts of the target site (that is, the bioadhesive matter) compete for the recognizing substances. Such dissociation would reverse the administered modified liposomes into regular, non-modified liposomes, thereby defeating the purpose of administration of the modified liposomes.

To form covalent conjugates of recognizing substances and liposomes, crosslinking reagents have been studied for effectiveness and biocompatibility. Once such reagent is glutaraldehyde (GAD). Through the complex chemistry of crosslinking by GAD, linkage of the amine residues of the recognizing substances and liposomes is established.

The crosslinking reagents can include glutaraldehyde (GAD) and a water soluble carbodiimide, preferably, 1-ethyl-3-(3-dimethylaminopropyl)carbodiimide (EDC). The recognizing substances include gelatin, collagen, and hyaluronic acid (HA). Following these methodologies, recognizing substances may be utilized as an adhesive or glue to attach the liposomes onto a target area, such as the lung.

Thus, while not essential to the instant invention, the use of such bioadhesive liposomes, particularly those having hyaluronic acid as the bioadhesive ligand, will potentially increase residence time in pulmonary sites, and reduce mucociliary clearance and macrophage uptake.

In general, ciprofloxacin is preferably used in the formulations of the instant invention, although other antibiotics or anti-infectives known to those skilled in the art may be used.

Multilamellar vesicles (MLV) are prepared according to techniques well known in the art. Briefly, in an embodiment, lipids are weighed and dissolved in a suitable organic solvent (such as chloroform or chloroform-methanol mixtures). The organic solvent is evaporated to complete dryness in a rotary evaporator, under low pressure, and at a temperature range of about 37-40° C. Following evaporation, the ciprofloxacin solution is added to the dry lipid film. The system is vigorously mixed, then incubated for about two hours in, for example, a shaker bath at a temperature range appropriate for the lipid composition. The preparation is then preferably buffered, for example, by adding about a one tenth volume of ten-fold concentrated phosphate buffered saline (PBS), of pH 7.4.

In an embodiment, MLV generated as described above serve as the source material for acidic unilamellar vesicles (ULV). For example, MLV are prepared as described above and subjected to extrusion in a device such as, for example, that manufactured by Lipex Biomembranes, Inc. (Vancouver, British Columbia).

Extrusion is performed through a series of membranes with progressively-smaller pore sizes, such as, for example, starting with pore sizes in the range of 0.8 to 1.0 μm (one to two extrusion cycles per pore size) and ending at the pore size range selected according to the desired liposome size (e.g., about seven cycles of extrusion at the final pore size).

Exemplary liposome compositions and methods of making them are disclosed in U.S. Pat. Nos. 6,890,555; 6,855,296; 6,770,291; 6,759,057; 6,623,671; 6,534,018; 6,355,267; 6,316,024; 6,221,385 and 6,197,333 all of which are incorporated herein by reference. The liposomes of the invention may be multilamellar, unilamellar, or any configuration known such as described in the above patents. The liposomes of the instant invention are preferably made from biocompatible lipids. In general, the size of the liposomes generated is over a wide range depending on mode of delivery, e.g. 1 nm to 10 μM or 20 nm to 1 μm or about 100 nm in diameter ±20% for pulmonary delivery.

II. Pharmaceutical Formulation of Ciprofloxacin-containing Liposomes

In a preferred embodiment, the liposome-encapsulated ciprofloxacin is administered to a patient in an aerosol inhalation device but could be administered by the IV route. In some embodiments, ciprofloxacin is encapsulated in the liposomes in combination with other pharmaceuticals that are also encapsulated. In some embodiments, ciprofloxacin is encapsulated in the liposomes in combination with other pharmaceuticals that are not encapsulated. In some embodiments, the liposomes are administered in combination with ciprofloxacin that is not encapsulated, with pharmaceuticals that are not encapsulated, or various combinations thereof.

Formulations of the invention can include liposomes containing ciprofloxacin in combination with an amount of alveolar surfactant protein effective to enhance the transport of the liposomes across the pulmonary surface and into the circulatory system of the patient. U.S. Pat. No. 5,006,343, issued Apr. 9, 1991, which is incorporated herein by reference, disclosed liposomes and formulations of liposomes used in intrapulmonary delivery. The formulations and methodology disclosed in U.S. Pat. No. 5,006,343 can be adapted for the application of ciprofloxacin and may be included within the delivery device of the present invention in order to provide for effective treatments of cystic fibrosis patients.

Regardless of the form of the drug formulation, it is preferable to create droplets or particles for inhalation in the range of about 0.5 µm to 12 µm, preferably 1 µm to 6 µm, and more preferably about 2-4 µm. By creating inhaled particles which have a relatively narrow range of size, it is possible to further increase the efficiency of the drug delivery system and improve the repeatability of the dosing. Thus, it is preferable that the particles not only have a size in the range of 0.5 µm to 12 µm or 2 µm to 6 µm or about 3-4 µm but that the mean particle size be within a narrow range so that 80% or more of the particles being delivered to a patient have a particle diameter which is within ±20% of the average particle size, preferably ±10% and more preferably ±5% of the average particle size.

The formulations of the invention may be administered to a patient using a disposable package and portable, hand-held, battery-powered device, such as the AERx device (U.S. Pat. No. 5,823,178, Aradigm, Hayward, Calif.). Alternatively, the formulations of the instant invention may be carried out using a mechanical (non-electronic) device. Other inhalation devices may be used to deliver the formulations including conventional jet nebulizers, ultrasonic nebulizers, soft mist inhalers, dry powder inhalers (DPIs), metered dose inhalers (MDIs), condensation aerosol generators, and other systems. The proportion of free ciprofloxacin to encapsulated ciprofloxacin was shown to remain constant after nebulization; i.e., there was no damage to the liposomes during nebulization that would result in premature release of a portion of the encapsulated antibiotic. This finding is unexpected based upon prior literature reports (Niven R W and Schreier H, 1990) but ensures that the animal or human inhaling the aerosol will get a reproducible proportion of free to encapsulated drug depositing throughout the lung.

An aerosol may be created by forcing drug through pores of a membrane which pores have a size in the range of about 0.25 to 6 microns (U.S. Pat. No. 5,823,178). When the pores have this size the particles which escape through the pores to create the aerosol will have a diameter in the range of 0.5 to 12 microns. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that an object of some embodiments is to provide aerosolized particles having a diameter in the range of about 0.5 to 12 microns.

The liposome formulation may be a low viscosity liquid formulation. The viscosity of the drug by itself or in combination with a carrier should be sufficiently low so that the formulation can be forced out of openings to form an aerosol, e.g., using 20 to 200 psi to form an aerosol preferably having a particle size in the range of about 0.5 to 12 microns.

In an embodiment, a low boiling point, highly volatile propellant is combined with the liposomes of the invention and a pharmaceutically acceptable excipient. The liposomes may be provided as a suspension or dry powder in the propellant, or, in another embodiment, the liposomes are dissolved in solution within the propellant. Both of these formulations may be readily included within a container which has a valve as its only opening. Since the propellant is highly volatile, i.e. has a low boiling point, the contents of the container will be under pressure.

In accordance with another formulation, the ciprofloxacin-containing liposomes are provided as a dry powder by itself, and in accordance with still another formulation, the ciprofloxacin-containing liposomes are provided in a solution formulation. The dry powder may be directly inhaled by allowing inhalation only at the same measured inspiratory flow rate and inspiratory volume for each delivery. The powder may be dissolved in an aqueous solvent to create a solution which is moved through a porous membrane to create an aerosol for inhalation. Any formulation which makes it possible to produce aerosolized forms of ciprofloxacin-containing liposomes which can be inhaled and delivered to a patient via the intrapulmonary route may be used in connection with the present invention. Specific information regarding formulations which can be used in connection with aerosolized delivery devices are described within Remington's Pharmaceutical Sciences, A. R. Gennaro editor (latest edition) Mack Publishing Company. Regarding insulin formulations, it is also useful to note the findings of Sciarra et al., (1976). When low boiling point propellants are used, the propellants are held within a pressurized canister of the device and maintained in a liquid state. When the valve is actuated, the propellant is released and forces the active ingredient from the canister along with the propellant. The propellant will "flash" upon exposure to the surrounding atmosphere, i.e., the propellant immediately evaporates. The flashing occurs so rapidly that it is essentially pure active ingredient which is actually delivered to the lungs of the patient.

III. Dosing Regimens

Based on the above, it will be understood by those skilled in the art that a plurality of different treatments and means of administration can be used to treat a single patient. Thus, patients already receiving such medications, for example, as intravenous ciprofloxacin or antibiotics, etc., may benefit from inhalation of the formulations of the present invention. Some patients may receive only ciprofloxacin-containing liposome formulations by inhalation. Such patients may have symptoms of cystic fibrosis, be diagnosed as having lung infections, or have symptoms of a medical condition, which symptoms may benefit from administration to the patient of an antibiotic such as ciprofloxacin. The formulations of the invention may also be used diagnostically. In an embodiment, for example, a patient may receive a dose of a formulation of the invention as part of a procedure to diagnose lung infections, wherein one of more of the patient's symptoms improves in response to the formulation.

A patient will typically receive a dose of about 0.01 to 10 mg/kg/day of ciprofloxacin ±20% or ±10%. This dose will typically be administered by at least one, preferably several "puffs" from the aerosol device. The total dose per day is preferably administered at least once per day, but may be divided into two or more doses per day. Some patients may benefit from a period of "loading" the patient with ciprofloxacin with a higher dose or more frequent administration over a period of days or weeks, followed by a reduced or maintenance dose. As cystic fibrosis is typically a chronic condition, patients are expected to receive such therapy over a prolonged period of time.

It has previously been shown that inhalation of liposome-encapsulated fluoroquinolone antibiotics may be effective in treatment of lung infections and were shown to be superior to the free or unencapsulated fluoroquinolone in a mouse model of *F. tularensis* (CA 2,215,716, CA 2,174,803 and CA 2,101,241). However, they did not anticipate the potential benefit of combining the free and encapsulated fluoroquinolone antibiotics to treat those lung infections. According to one aspect of the present invention, high concentrations of an antibiotic are delivered immediately while also providing a sustained release of the therapeutic over hours or a day.

Another application, EP1083881B1, describes liposomes containing a drug-conjugate comprising a quinolone compound covalently attached to an amino acid. That application does not foresee the requirement to have both an immediate release and sustained release component to treat those lung infections.

Another application, US 2000142026, also describes the use of liposome-encapsulated antibiotics. That application discusses the potential for administration of a lower dose of a liposome-encapsulated antibiotic, by a factor of 10 or 100, than for the free unencapsulated antibiotic. However, they did not anticipate the benefit of combining both free and encapsulated antibiotic to provide an initially high therapeutic level of the antibiotic in the lungs to overcome the barrier to eradicating the difficult to treat biofilm bacteria.

Other applications describing the use of liposomes containing anti-infectives to treat cystic fibrosis, US 20060073198 and US 20040142026 show efficacy for a lower dose liposomal formulation compared to the use of the free drug alone.

Thus, as discussed above, the formulations according to some aspects of the invention include free or non-encapsulated ciprofloxacin in combination with the liposome-encapsulated ciprofloxacin. Such formulations may provide an immediate benefit with the free ciprofloxacin resulting in a rapid increase in the antibiotic concentration in the lung fluid surrounding the bacterial colonies or biofilm and reducing their viability, followed by a sustained benefit from the encapsulated ciprofloxacin which continues to kill the bacteria or decrease its ability to reproduce, or reducing the possibility of antibiotic resistant colonies arising. The skilled practitioner will understand that the relative advantages of the formulations of the invention in treating medical conditions on a patient-by-patient basis.

It has long been known that inhalation of fine particulate matter (PM) from environmental and occupational sources can be associated with an increase in respiratory symptoms including cough, wheeze, shortness of breath (Koren 1995), reduction in lung function (Pope et al., 1995), exacerbation of asthma (Choudhury et al., 1997) and COPD (Abbey et al, 1995), and even increased premature mortality. Nurkiewicz et al (2004) have shown that pulmonary exposure to fine PM impairs endothelium dependent dilation in systemic arterioles and more recently that ultrafine PM was more toxic by virtue of its increased surface area (2008). In those studies in rats, the principal histopathologic alterations in the lung consisted of particle accumulation within alveolar macrophages, the presence of a nuclear macrophages, and an intimate association between particle-laden alveolar macrophages and the alveolar wall. In addition to the particle accumulation, macrophages containing particles were frequently intimately associated with the alveolar wall a location, suggestive of, but not diagnostic of, macrophage activation. These results are consistent with long standing data that shows that particle delivery to the lung results in an increase in macrophages in rats (Yevich, 1965). The alveolar macrophages are phagocytic and provide an important defense mechanism against inhaled pathogens and clearing inhaled dust from the alveoli. However, if the level of exposure is too high, the macrophages can become sufficiently stimulated resulting in the secretion of mediators that cause inflammatory changes in the bronchoalveolar region.

The implication of these studies is that any particulate containing formulation, e.g., liposomes containing an anti-infective, may result in an increased particle load in the lung, stimulation of macrophages and the potential to cause inflammation and lung damage. Thus, it is important that the "particulate" formulation is safe and does not produce an excessive inflammatory response in the lung. As we describe in some aspects of the invention, the presence of free ciprofloxacin, or any free antibiotic with similar anti-inflammatory properties, in the formulation, in addition to providing an immediate high level of antibiotic to treat the lung infection, may also provide a mechanism to attenuate the lung's response to the inhaled liposome or particulate containing formulation; i.e., reduce macrophage influx and other cytokines.

IV. Other Formulations or Carriers

Although liposomes have been primarily described as the vehicle to provide encapsulation of the therapeutic and thus the sustained release effect, there is no intention to limit the formulation to liposomal formulations. A combination of immediate and sustained release formulations or carriers of an anti-infective in the lung may be achieved via a multitude of ways including microspheres, polymers, gels, emulsions, particulates or suspensions, either singly or in combination. Some formulations or carriers may have properties that result in closer association with the biofilm matrix and these may prove more advantageous with respect to increasing the therapeutic levels of the anti-infective proximal to the biofilm bacteria.

Viscous Controlled Release Formulations

An example of a sustained release polymer formulation is the use of poly(ortho esters) as the vehicle. For example, see U.S. Pat. Nos. 4,304,767, 4,957,998, 5,968,543 and WO 02/092661 as well as Adv. Polymer Sci., 107, 41-92 (1993) and references therein. Viscosities of these controlled release polymers were reported to be in the 1,500 cP range (see Biomaterials, 23, 2002, 4397-4404). Considerably higher forces were required for higher molecular weight polymers (see Adv. Drug Del Reviews, 53, 2001, 45-73).

Novel Liposomes

Various long-circulating liposomes have been prepared by incorporating glycolipids or other amphiphilic molecules into the lipid bilayer of conventional liposomes. Vasopressin entrapped in PEGylated long-circulating liposomes even remained bioactive one month after intravenous injection (Woodle et al., 1992).

A new approach, rather than using unilamellar or multilamellar liposomes, is based on the DEPOFOAM system. These multivesicular liposomes (1-100 μm) contain multiple non-concentric internal aqueous compartments and lead to an increase in the encapsulation efficiency. After subcutaneous injection, the release of encapsulated peptide and protein was shown to be prolonged up to 7 days for DepoInsulin and up to 3 weeks for the DepoLeuprolide® formulation (Ye, Q et al., 2000).

The company Novosom AG has patented a novel liposome-based depot system for proteins and peptides. The Cagicles® depots are produced by a two step method: first, proteins are dissolved in an aqueous medium and then added to solutions of membrane-forming substances, which are selected such that the resulting membrane enters into a reversible mutual reaction with the protein. This mild-condition process enables to increase the encapsulation rate over 30% of incorporated protein. Furthermore, a one month sustained protein release was feasible after subcutaneous or intramuscular injection of the Cagicles® depots (Panzner, S., Novosom A G, Application No. 2000-EP11079, WO 2001034115 (2000)). These studies have proven the basic applicability of liposomes. The solubility benefits of liposomes are well known and reported.

Lipid Nanoparticles and Microspheres

Solid lipid nanoparticles (SLNs) represent a colloidal carrier system mainly based on triglycerides. Due to their hydrophobic nature and their small size, SLNs may be more appropriate for incorporation of lipophilic drugs, which can be easily dissolved in the melted mixture. For instance, only small quantities of lysozyme can be incorporated into various lipids (Almeida et al., 1997). Solid lipid nanoparticles own potential for the encapsulation of drugs with a low solubility (e.g. paclitaxel), for the application of surface-modified SLNs in drug targeting, or maybe for the use as adjuvant for vaccines. Furthermore, it can be hypothesised that SLNs can be applied for oral drug delivery in the form of aqueous dispersions or that they can alternatively be used as additives in traditional dosage forms such as tablets, capsules or pellets.

U.S. Pat. No. 6,277,413 describes a biodegradable microsphere having a matrix, the matrix comprising at least one type of biodegradable polymer, and at least one type of lipid; and a physiologically active substance which is releasable from the biodegradable microsphere.

Lipid Crystals

EP 0767,656B1 describes a pharmaceutical composition, which is glycerol-ester based and contains diacyl glycerol as well as phospholipid(s), or a polar group containing water, glycerol, ethylene glycol or propylene glycol. The proportions between the components are adjusted to form an L2 phase or a liquid crystalline phase, with the biological material being dispersed or dissolved in the L2 or liquid crystalline phase.

Oil Suspensions

Generally, the viscosity of oily media is considerably higher than the viscosity of an aqueous phase such as buffer. Therefore, drug release can be prolonged by implementing oil suspensions. In addition, the viscosity of the oily carrier may be further increased by the addition of gelling agents such as aluminum monostearate—thus enabling the control of process parameters like drug solubility and drug transfer rate. A further important aspect using oils as drug carrier refers to the distribution coefficient of compounds in the oily medium and the surrounding tissue. A lipophilic drug with a high distribution coefficient will primarily accumulate in the oily medium resulting in further deceleration of effective drug actions.

For several years, various peptides and proteins have been dispersed in oils to engineer sustained-release formulations. Nestor et al. patented as early as 1979 the development of long-acting injectable depot formulations for super-agonist analogues of luteinizing hormone-releasing hormone (LH-RH), applying oils such as peanut oil or sesame oil and a gelling agent such as aluminum stearate (Nestor et al., Syntex Inc., U.S. Pat. No. 4,256,737 (1979)).

Hydrogels

Thermoreversible hydrogels are of great interest in drug delivery. These include thermosensitive gel materials including poly(ethylene glycol)/poly(propylene glycol) block copolymers (poloxamers), poly(ethylene glycol)/poly(butylenes glycol) block copolymers, poloxamer-g-poly(acrylic acid) and copolymers of Nisopropylacrylamide that exhibit a sol-to-gel transition in aqueous solutions. Diblock copolymers of poly(ethylene oxide) (PEG) and poly(lactic acid) (PLA), and triblock copolymers of PEG-PLGA-PEG are also used as alternative hydrogels that would provide biodegradable and injectable drug-delivery systems under physiological conditions. Some natural polymers including gelatin, agarose, amylase, amylopectin, cellulose derivatives, carrageenans, and gellan, exhibit thermoreversible gelation behavior. Some cellulose derivatives of natural polymers, such as methyl cellulose and hydroxypropyl cellulose, exhibit reverse thermogelation behavior (gelation at elevated temperatures). Viscosity of these hydrogels is a concern for parenteral delivery. Viscosity of these hydrogels can be extremely high at low shear rates (Thorgeirsdottir T O et al., 2005). Poly hydroxyl methacralate is extensively used in hydrogel formulations (Peppas et al., 2000). U.S. Pat. No. 6,602,952 describes a polymeric structure comprising a multifunctional poly(alkylene oxide), such as a poly(ethylene glycol) derivative, covalently cross-linked to a polymer selected from the group consisting of chitosan and conjugates of chitosan and a monofunctional poly(alkylene oxide), such as methoxy poly(ethylene glycol). In aqueous media, the polymeric structure forms a hydrogel.

Depot Formulations

Implantable drug delivery devices provide an attractive therapeutic tool for treatment of a variety of diseases and conditions, especially when a sustained release effect is also added to the therapy. Various implantable drug delivery devices have been developed, and are based upon different mechanisms to accomplish movement of drug from a reservoir to the treatment site. U.S. Pat. No. 4,938,763 discloses a method for forming an implant in situ by dissolving a nonreactive, water insoluble thermoplastic polymer in a biocompatible, water soluble solvent to form a liquid, placing the liquid within the body, and allowing the solvent to dissipate to produce a solid implant. U.S. Pat. No. 5,747,058 describes a composition for the controlled release of substances that includes a non-polymeric non-water soluble high-viscosity liquid carrier material of viscosity of at least 5,000 cP at body temperature that does not crystallize neat under ambient or physiological conditions.

Delivery of Macromolecules

The addition of a protein or peptide drug to the anti-infective formulation may provide additional therapeutic benefit. A previously discussed example includes Pulmozyme rhDNase which is approved in the treatment of CF. While some macromolecules may be delivered at a low dose or at relatively low concentrations, for others it may be necessary to deliver at high concentrations. Protein formulations at high concentrations may have physical properties that impact the ability to easily deliver the protein drug. U.S. Pat. No. 6,541,606 describes protein crystals or crystal formulations that are encapsulated within a matrix comprising a polymeric carrier to form a composition. The formulations and compositions enhance preservation of the native biologically active tertiary structure of the proteins and create a reservoir which can slowly release active protein where and when it is needed.

Conjugated Systems

Polymer carrier systems may have certain advantages over non-polymeric carriers in terms of avoiding uptake by macrophages. Because liposomes are spherical vesicles made of phospholipids are particles, they get taken up by macrophages. High levels can be found in the liver and spleen, even when the liposomes are given "stealth" characteristics by coating them with PEG. Antibodies, meanwhile, have the disadvantage that most receptors on tumor cells are also present on normal cells, making it hard to find ones that are unique to cancer.

In contrast, water-soluble polymers allow working with a single molecule rather than a large particle. To avoid the liver and spleen, uncharged hydrophilic polymers, such as PEG and N-(2-hydroxypropyl)methacrylamide can be used. When these polymers are hydrated, they can circulate in the blood for periods of up to about 24 hours (C&E News, Volume 80, Number 34, 39-47).

Examples of other conjugated systems include PEGylation. PEGylation decreases the rate of clearance from the bloodstream by increasing the apparent molecular weight of the molecule. Up to a certain size, the rate of glomerular filtration of proteins is inversely proportional to the size of the protein. Decreased clearance can lead to increased efficiency over the non-PEGylated material (Conforti et al. 1987 and Katre et al. 1987). The conjugation could be either in-vitro or in-vivo.

WO2005034909A2 describes a hyperbranched polymer attached to a core and a biologically active moiety. The biologically active moiety is attached to the core by means of a substantially non-enzymatically cleavable linker L. The composition can be used to deliver the biologically active moiety to its target.

U.S. Pat. No. 6,946,134 describes therapeutic proteins fused to albumin or fragments or variants of albumin, that exhibit extended shelf-life and/or extended or therapeutic activity in solution. The role of albumin as a carrier molecule and its inert nature are desirable properties for use as a carrier and transporter of polypeptides in vivo. The use of albumin as a component of an albumin fusion protein as a carrier for various proteins has been suggested in WO93/15199, WO93/15200, and EP413622. The use of N-terminal fragments of HA for fusions to polypeptides has also been proposed (EP399666).

U.S. Pat. No. 5,367,051 describes fullerene-functionalized amine-containing polymers and polymerizable monomers characterized by high temperature stability, i.e., capable of withstanding a temperature of at least about 300° C., when in polymerized form. The fullerene groups are bonded to the polymers through the amine groups on the polymer.

WO Patent No. 2005073383 describes novel heterodimeric fusion proteins comprising a first polypeptide including an alpha subunit of FSH (aFSH) linked directly or indirectly to a binding partner of neonatal Fc receptor (FcRn) and a second polypeptide including a beta subunit of FSH (βFSH) linked directly or indirectly to an FcRn binding partner. The conjugated polypeptide has increased half-life and bioavailability as compared to traditional forms of FSH therapy.

Dendrimers

Dendrimers are well-defined polymeric structures. Dendrimers are based on repeating hyperbranched structures emanating from a central core (U.S. Pat. No. 4,507,466). Typical dendrimers are based on polyamidoamine (PAMAM), polyethylene imine (PEI), polypropylene imine or polylysine. These synthetic macromolecules are assembled in a stepwise fashion, with each reaction cycle adding another layer of branches (dubbed "generation"). Dendrimers are synthetically accessed by stepwise, divergent "bottom-up" or convergent "top-down" synthesis. Central structural component is the core unit from which hyperbranched dendrimers extend in a radially symmetric fashion. The core may provide at least two reactive groups for dendrimer conjugation, it may also be of heterofunctional nature and protecting groups may be used. In the latter case, the dendrimer may be assembled, and a guest compound may be subsequently conjugated to an anilin core by means of orthogonal chemistries (WO88/01180). The core and dendrimers form the interior or backbone of a dendrimer. As a consequence of the spherical symmetry supported by sterical crowding, the terminal groups of the hyperbranches are defining the exterior. In higher generation dendrimers, the terminal branches form rather dense shells and flexible internal voids have been discovered. It is understood, that for a given dendrimer these cavities are filled up by backfolded end groups and tightly coordinated solvent molecules. Dendrimers are related to micelles, similarly well suited to complex hydrophobic compounds. But in contrast they exhibit higher structural order because of their monomolecular nature and the absence of a dynamic equilibrium of various species. Synthetic compounds can only diffuse into dendrimers if certain structural requirement such as conformational rigidity and flatness as well as charge distribution such as affinity to tertiary amines are met. Various apolar compounds such as pyrene or naphthalene have been encapsulated in dendrimers.

In U.S. Pat. No. 5,714,166 and WO95/24221, dendrimer-protein conjugates are revealed. PAMAM dendrimers of G4 are covalently coupled through their terminal functional groups to insulin, fluorescently labeled insulin, avidin, monoclonal antibodies and bradykinin. The reactive groups used for conjugation are only present at the surface of the dendrimers, and therefore any covalent adduct generated by the leached method will be associated with the dendrimer exterior.

PAMAM dendrimers contain free amine groups on their surfaces and readily associate with DNA through electrostatic interactions.

WO01/07469 details water-soluble polypeptide dendrimers constituted of ornithin and glycine amino acids. The patent application also teaches the non-covalent encapsulation of an oligosaccharide, heparin, by dendrimerization of the dendrimer core in presence of heparin under mild conditions. The oligosaccharide is released from the dendrimer by light-induced cleavage of W-labile bonds within the dendritic backbone. The core structure used here was tris(2-maleimidoethyl) amine. Other Polymeric Systems The use of heparin, dextran and methyl methacralate in a biomimetric approach was evaluated in the development of drug carriers escaping early capture by phagocytosis (Passirani et al., 1998).

The synthesis of hybrid block and graft copolymers of polyphosphazenes and polystyrene is a way to combine the attributes of both polymers and generate new properties. Many of the valuable properties of the respective phosphazene and styrene homopolymers can be combined without sacrificing the overall solid state or solution properties of both polystyrene and polyphosphazene polymers. U.S. Pat. No. 6,392,008 describes such compositions of polyphosphazene-containing polymers.

U.S. Pat. No. 5,176,907 describes biocompatible and biodegradable poly(phosphoester-urethanes), compositions comprising the poly(phosphoester-urethanes), and methods of use as a drug delivery device and an implant.

V. Combination Therapies

Liposome formulations of the invention may be administered concurrently with other drugs as described here. For example, the liposomes of the invention may be used along with drugs such as DNase, a mucolytic agent, chemicals that up-regulate the chloride ion channel or increase flow of ions across the epithelial surface of cells, a bronchodilator, a steroid, a P2Y2 agonist, an elastase inhibitor such as Alpha-1 antitrypsin (AAT), N-acetylcysteine, agents that enhance the activity of the antibiotic against biofilm bacteria such as sodium salicylate, interferon gamma, interferon alpha, or a fluoroquinolone selected from the group consisting of amifloxacin, cinoxacin, ciprofloxacin, danofloxacin, difloxacin, enoxacin, enrofloxacin, fleroxacin, irloxacin, lomefloxacin, miloxacin, norfloxacin, ofloxacin, pefloxacin, rosoxacin, rufloxacin, sarafloxacin, sparfloxacin, temafloxacin and tosufloxacin or an antibiotic selected from the group of tobramycin, colistin, azithromycin, amikacin, cefaclor (Ceclor), aztreonam, amoxicillin, ceftazidime, cephalexin (Keflex), gentamicin, vancomycin, imipenem, doripenem, piperacillin, minocycline, or erythromycin.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

VI. Method of Treatment

Until now we have discussed primarily the application of this invention to treat infections in cystic fibrosis patients. However, it will be obvious to one skilled in the art that this invention will have utility and advantages beyond CF. This method of treatment applies to other disease states which involve infections of the nasal passages, airways, inner ear, or lungs; including but not limited to: bronchiectasis, tuberculosis, pneumonia; including but not limited to ventilator associated pneumonia, community acquired pneumonia, bronchial pneumonia, lobar pneumonia; infections by *Streptococcus pneumoniae*, *Chlamydia*, *Mycoplasma* pneumonia, staphylococci, prophylactive treatment or prevention for conditions in which infection might arise, e.g., intubated or ventilated patients, infections in lung transplant patient, bronchitis, pertussis (whooping cough), inner ear infections, streptococal throat infections, inhalation anthrax, tularemia, or sinusitis.

EXPERIMENTAL

The following examples are put forth so as to provide those of ordinary skill in the art with a complete disclosure and description of how to make and use the present invention, and are not intended to limit the scope of what the inventors regard as their invention nor is it intended to represent that the experiment below is the only experiment performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Manufacture of Encapsulated Ciprofloxacin:

Ciprofloxacin (50 mg/mL) is encapsulated into liposomes consisting of hydrogenated soy phosphatidyl-choline (HSPC) (70.6 mg/mL), a semi-synthetic fully hydrogenated derivative of natural soy lecithin (SPC), and cholesterol (29.4 mg/mL). The lipid is organized in a bilayer, with an average particle size of 75 to 120 nm. The sterile suspension is suspended in an isotonic buffer (25 mM histidine, 145 mM NaCl at pH 6.0, 300 mOsm/kg) and administered by inhalation. These liposomal ciprofloxacin preparations contained approximately 1% unencapsulated ciprofloxacin.

The manufacturing process includes the following steps.
1. Preparation of buffers.
2. Weighing of lipid components.
3. Dissolution of lipids in solvent (tBuOH:EtOH:dH2O/49:49:2).
4. Mixing of the solvent solution of lipids with methylamine sulphate buffer (10% v/v solvent) to form multilamellar vesicles (MLVs) with encapsulated methylamine sulphate buffer at 30 mg/mL lipid.
5. Extrusion through four stacked 80 nm pore size polycarbonate filters to generate large unilamellar vesicles (LUVs). A second extrusion pass was performed to generate liposomes with a mean diameter of ~100 nm.
6. Ultrafiltration to concentrate the liposomes to ~55 mg/mL total lipid.
7. Diafiltration against 10 volumes of buffer (145 mM NaCl, 5 mM histidine, pH 6.0) to remove ethanol and generate a transmembrane pH gradient.
8. Determination of the lipid concentration by HPLC.
9. Heating of the liposome suspension to 50° C. and slow addition of powdered ciprofloxacin (60% of the total lipid mass) with stirring. Ciprofloxacin is added incrementally (10% of mass every 4 minutes over a 40-minute period) and the product incubated at 50° C. for 20 minutes following addition of the last aliquot to allow completion of the drug loading process.
10. Diafiltration of the ciprofloxacin loaded liposomes against 3-volumes of 145 mM NaCl, 5 mM acetate, pH 4.0 to remove unencapsulated ciprofloxacin under conditions in which the free ciprofloxacin is soluble.
11. Diafiltration of the ciprofloxacin loaded liposomes against 5-volumes of 145 mM NaCl, 25 mM histidine, pH 6.0 to remove any remaining un-encapsulated ciprofloxacin, further reducing the residual solvent levels and exchanging the external buffer for the desired final product buffer.
12. Ultrafiltration of the formulation to a ciprofloxacin concentration of 50 mg/mL (in-process testing required).
13. Pre-filtration of the liposomes through 0.45/0.2 μm filter sheets to remove particulates which can clog sterilizing grade filters. The filters employed are in fact sterilizing grade filters; however they are employed at elevated pressures not compatible with their use for sterile filtration.
14. Redundant filtration through 0.2 μm sterilizing grade filters.
15. Sample vialing and packaging.

The overall manufacturing scheme is shown in FIG. 1.

Description of Infection Model:

The ciprofloxacin encapsulated liposomes were evaluated in a mouse model of *P. aeruginosa* lung infection. The gut-corrected, Cftr knockout mice have been shown to have a cystic fibrosis lung phenotype following infection with *P. aeruginosa*-laden agarose beads (van Heeckeren et al., 2004), and have a similar inflammatory response as the UNC Cftr knockout mice (van Heeckeren et al., 2004). All of these features make this the strain of choice to investigate whether the drug has efficacy in a mouse model of cystic fibrosis lung infection, and not if there is a differential response between wild type and cystic fibrosis mice. Mice of one sex, male, were used to eliminate sex as a potential confounder. All mice were between 6-8 weeks of age and weighed >16 g.

*P. aeruginosa-laden* agarose (PA) beads were made and used, as described previously (van Heeckeren, et al., 1997, van Heeckeren et al., 2000, van Heeckeren and Schluchter, 2002), with minor differences. Mice were inoculated with a 1:35 dilution of the beads, and beads were delivered in mice anesthetized with isoflurane. This was established to be an LD50 dose, though subtle differences from experiment to experiment may lead to differential responses, which is not predictable. That is, in one experiment the dose is an LD50, but it may be an LD90 in another. Since we are interested in investigating whether these drugs have clinical efficacy, we attempted to dose between the LD50 and the LD90 range in infected CF control mice. Interventional euthanasia was performed if the mice were moribund (severe delay in the righting reflex and palpably cold), and a necropsy performed to determine whether there was overt lung infection. Mice that were sacrificed were included as if spontaneous death had occurred.

Liposomal Ciprofloxacin Treatments:

Formulations of liposomal ciprofloxacin or sham (diluent) (<0.05 ml) were delivered intranasally.

Design of Dose-ranging Study:

Three doses were tested: 10%, 33%, and 100% of full strength (50 mg/ml) ciprofloxacin composed of 99% encapsulated and 1% free ciprofloxacin, plus the liposomal diluent as a negative control. The low- and mid-dose were prepared by dilution. On Day 0, mice were inoculated transtracheally with *P. aeruginosa*-laden agarose beads diluted 1:35 in sterile PBS, pH 7.4. On Days 2 through 9, mice were treated with the drug or diluent sham once daily. On Day 10, mice were sacrificed. The outcome measures included clinical signs (including coat quality, posture, ability to right themselves after being placed in lateral recumbency, ambulation), changes from initial body weight, and survival. At the time of sacrifice, gross lung pathology was noted, bronchoalveolar lavage (BAL) was performed using 1 ml sterile PBS, pH 7.4, whole blood, unprocessed BAL fluid and spleen homogenates were tested for presence or absence of *P. aeruginosa*, and BAL cells were enumerated using a hemacytometer.

Figure 2:
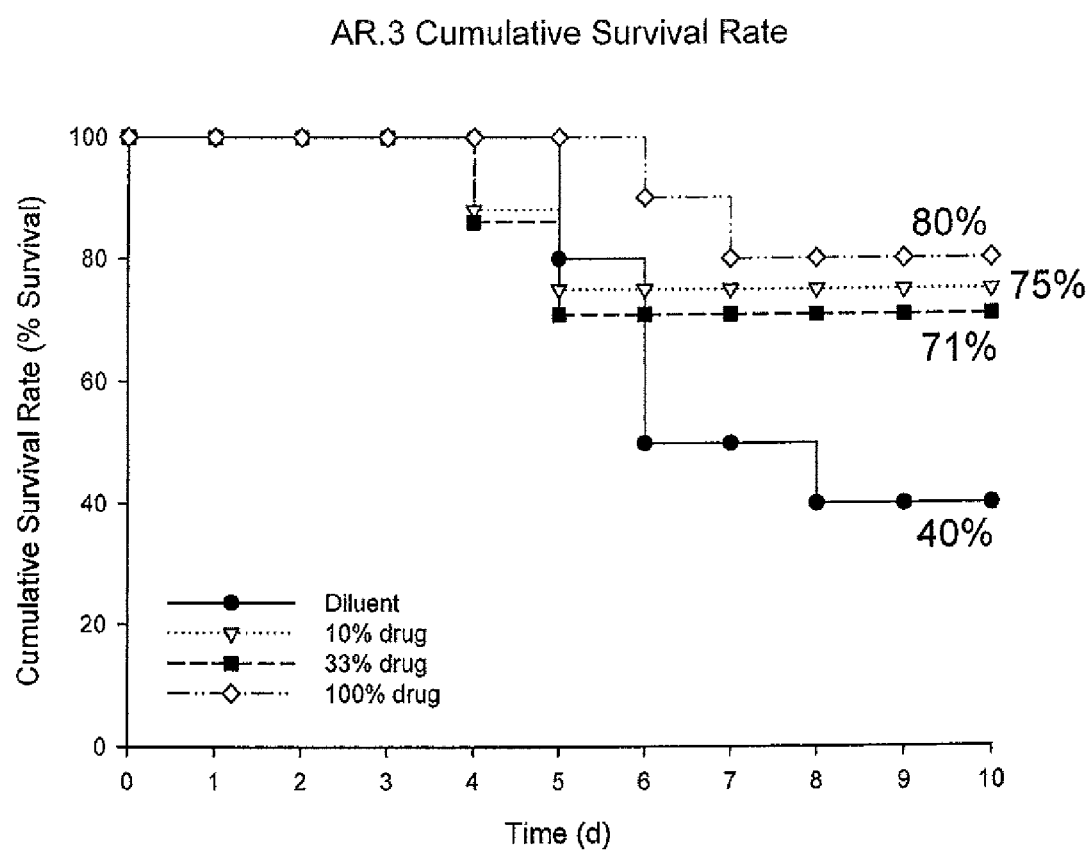
FIG. 2 is a graph showing the cumulative survival rate of mice following infection with *P. aeruginosa*-laden agarose beads on Day 0. Mice were treated intranasally once daily starting on Day 2 and ending on Day 9 with the liposomal formulation of ciprofloxacin (drug) at one of three different concentrations (100%, open diamond; 33%, closed square; or 10%, open triangle). Diluent was used as a control (closed circle). Surviving mice were sacrificed on Day 10.

Survival Results:

FIG. 2 shows the cumulative survival rate for each group out to 10 days reported as a percentage of the number of mice that survived. At Day 10, the three groups treated with liposomal ciprofloxacin had greater survival rates than the diluent control group. There were only 2 deaths in each of the liposomal treatment groups, whereas there were 6 deaths in the diluent group. The 100%-dose group had the longest survival of all the groups, with all mice surviving out to Day 5, whereas the other groups all had 2 deaths by this time.

Intranasal administration (to target the lung) of liposome-encapsulated ciprofloxacin containing approximately 1% free ciprofloxacin increased the survival rate of mice with *P. aeruginosa* lung infections. Accordingly, inhaled liposomal ciprofloxacin is efficacious in patients with cystic fibrosis, or other diseases with lung infections.

FIG. 2 shows the cumulative survival rate following infection. Mice were infected with *P. aeruginosa-laden* agarose beads on Day 0. Mice were treated intranasally once daily starting on Day 2 and ending on Day 9 with the liposomal formulation of ciprofloxacin (drug) at one of three different concentrations (100%, open diamond; 33%, closed square; or 10%, open triangle). Diluent was used as a control (closed circle). Surviving mice were sacrificed on Day 10.

Example 2

Preparation of Unencapsulated Ciprofloxacin: A solution of unencapsulated, or "free" ciprofloxacin at a concentration of 30 mg/mL in 10 mM sodium acetate, pH 3.2, was prepared.

Manufacture of encapsulated ciprofloxacin: Ciprofloxacin (50 mg/mL) was encapsulated into liposomes consisting of hydrogenated soy phosphatidyl-choline (HSPC) (70.6 mg/mL), a semi-synthetic fully hydrogenated derivative of natural soy lecithin (SPC), and cholesterol (29.4 mg/mL), as described in Example 1. Characterization of this liposomal formulation indicated that approximately 1% of the ciprofloxacin was free; that is, it was not encapsulated within the liposome.

Description of infection model: Formulations containing free ciprofloxacin and liposome encapsulated ciprofloxacin were evaluated in two additional experiments in a mouse model of *P. aeruginosa* lung infection as described in Example 1.

Design of dose-ranging study: One dose of the combination of free and liposomal ciprofloxacin (0.36 mg/kg free and 0.6 mg/kg liposomal ciprofloxacin), two doses of liposomal ciprofloxacin (0.6 mg/kg and 1.2 mg/kg) and the liposomal diluent as a negative control were evaluated in two separate experiments. On Day 0, mice were inoculated transtracheally with *P. aeruginosa*-laden agarose beads diluted 1:35 in sterile PBS, pH 7.4. On Days 2 through 9, mice were treated with the drug or diluent sham once daily. On Day 10, mice were sacrificed. The outcome measures included clinical signs (including coat quality, posture, ability to right themselves after being placed in lateral recumbency, ambulation), changes from initial body weight, and survival. At the time of sacrifice, gross lung pathology was noted, bronchoalveolar lavage (BAL) was performed using 1 ml sterile PBS, pH 7.4, whole blood, unprocessed BAL fluid and spleen homogenates were tested for presence or absence of *P. aeruginosa*, and BAL cells were enumerated using a hemacytometer.

Survival Results: Table 1 shows the cumulative survival rate for each group out to 10 days reported as a percentage of the number of mice that survived from both studies. At Day 10, all groups treated with a combination of free and liposomal ciprofloxacin had greater survival rates than the diluent control group.

TABLE 1

Mean survival per group from two studies in CF mice with *P. aeruginosa* lung infection treated with intranasally instilled ARD-3100, or control

| Dose (mg/kg) | % Free Ciprofloxacin | Mean Starting Number | Mean Mortality | Mean Survival (%) |
|---|---|---|---|---|
| 0 (Control) | N/A | 9 | 6/9 | 34% |
| 0.6 | 1 | 8.5 | 2.5/8.5 | 66% |
| 1.2 | 1 | 8.5 | 3/8.5 | 65% |
| 0.96 | 38 | 10.5 | 2.5/10.5 | 76% |

Conclusion: Intranasal administration (to target the lung) of liposome-encapsulated ciprofloxacin increased the survival rate of mice with *P. aeruginosa* lung infections. Inhaled liposomal ciprofloxacin or combinations of free and liposomal ciprofloxacin are efficacious in patients with cystic fibrosis, or other diseases with lung infections.

Example 3

Manufacture of encapsulated ciprofloxacin: Ciprofloxacin (50 mg/mL) was encapsulated into liposomes consisting of hydrogenated soy phosphatidyl-choline (HSPC) (70.6 mg/mL), a semi-synthetic fully hydrogenated derivative of natural soy lecithin (SPC), and cholesterol (29.4 mg/mL), as described in Example 1. Characterization of this liposomal formulation indicated that approximately 1% of the ciprofloxacin was free; that is, it was not encapsulated within the liposome.

Delivery of Combination of Free and Encapsulated Ciprofloxacin: Rather than using a formulation which contains both free and encapsulated ciprofloxacin, an alternative method is to create the mixture during the delivery event. For example, the addition of shear or heat in a controlled fashion may reproducibly result in some of the liposomes losing their integrity and releasing the contents of drug that were previously encapsulated within the liposomes. Studies using the electromechanical AERx system confirmed the possibility of using this approach. Formulations containing approximately 99% encapsulated ciprofloxacin were delivered using the AERx system and the aerosol droplets were collected. With the temperature controller set at temperatures of 13, 45, 77, 108 and 140° C. the collected aerosol contained 89, 84, 82, 77 and 41 percent encapsulated, respectively.

The instant invention is shown and described herein in a manner which is considered to be the most practical and preferred embodiments. It is recognized, however, that departures may be made therefrom which are within the scope of the invention and that obvious modifications will occur to one skilled in the art upon reading this disclosure.

While the instant invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 4

Manufacture of encapsulated ciprofloxacin: Ciprofloxacin (50 mg/mL) was encapsulated into liposomes consisting of hydrogenated soy phosphatidyl-choline (HSPC) (70.6 mg/mL), a semi-synthetic fully hydrogenated derivative of natural soy lecithin (SPC), and cholesterol (29.4 mg/mL), as described in Example 1. Characterization of this liposomal formulation indicated that approximately 1% of the ciprofloxacin was free; that is, it was not encapsulated within the liposome.

Manufacture of Unencapsulated (or free) Ciprofloxacin: Under aseptic manufacturing conditions, ciprofloxacin-HCl as powder was dissolved in 10 mM sodium acetate solution, pH 3.3 and sterile filtered resulting in a 24 mg/mL solution.

Delivery of Combination of Free and Encapsulated Ciprofloxacin: In this example the free and encapsulated formulations are mixed in the nebulizer and delivered as aerosol at the time of administration. The pH of the resulting mixture is between 4.0 and 5.0. Samples of the delivered aerosol and the solution remaining in the nebulizer following aerosolization (i.e., the nebulizer residual) were analyzed to ensure that the mixing and nebulization process did not degrade the integrity of the liposomes. No loss in encapsulated ciprofloxacin was observed. This result ensures that a precise and reproducible amount of free and encapsulated ciprofloxacin is delivered to the human subject or patient, or animals during preclinical safety or preclinical efficacy studies.

Evaluation of the Free and Encapsulated Ciprofloxcain in a 14-Day Nose-Only Inhalation Toxicology Study in Sprague Dawley Rats: Various ciprofloxacin formulations were evaluated in this 28 day inhalation toxicology study with 28 and 56 day recovery arms. Exposure to nebulized liposomal ciprofloxacin by nose-only inhalation for 6 hours per day, 7 days per week for 14 days at a target pulmonary dose of 8.2 (Low), or 16.5 (High) mg/kg/day resulted in histopathology findings in the lung (focal macrophage accumulation, and alveolar wall monocyte infiltration) at the end of the 14 day exposure period. After a 28-day recovery period, histopathology findings were still present in the lung (focal macrophage accumulation, and alveolar wall monocyte infiltration, Table II).

Evaluation of the Free and Encapsulated Ciprofloxcain in a 28-Day Nose-Only Inhalation Toxicology Study in Sprague Dawley Rats: Various ciprofloxacin formulations were evaluated in this 28 day inhalation toxicology study with 28 and 56 day recovery arms. Exposure to nebulized liposomal ciprofloxacin by nose-only inhalation for 6 hours per day, 7 days per week for 28 days at a target pulmonary dose of 11 (Low), 21 (Mid), or 31 (High) mg/kg/day resulted in histopathology findings in the lung (diffuse macrophage accumulation, focal macrophage accumulation, and alveolar wall monocyte infiltration) at the end of the 28 day exposure period. After a 28-day recovery period, histopathology findings were still present in the lung (focal macrophage accumulation, and alveolar wall monocyte infiltration, Table II). After a 56 day recovery period, histopathology findings were still present in the lung for all three groups exposed to liposomal ciprofloxacin (focal macrophage accumulation, and alveolar wall monocyte infiltration, alveolar wall fibrosis and crystal formation in alveolar lumens, Table III).

TABLE II

Recovery Necropsy (after 28-day recovery)

| Organ | Lesion | Sex | Saline 0 mg/kg | Low 14-day 8.2 mg/kg | Low 28-day 11 mg/kg | High 14-day 16.5 mg/kg | Mid 28-day 21 mg/kg | High 28-day 31 mg/kg | Mixture 14-day 11.5 mg/kg | Mixture 28 day 34 mg/kg |
|---|---|---|---|---|---|---|---|---|---|---|
| | | | | | | Incidence (group mean severity score) | | | | |
| Lung | Focal macrophage accumulation | M | 0/5 (0.00)* | 2/5 (0.40) | 3/5 (0.60) | 5/5 (1.40) | 5/5 (2.60) | 5/5 (2.80) | 1/5 (0.20) | 3/5 (0.60) |
| | Focal macrophage accumulation | F | 2/5 (0.40) | 4/5 (0.80) | 5/5 (2.40) | 5/5 (1.20) | 5/5 (2.60) | 5/5 (3.00) | 0/5 | 5/5 (1.60) |

TABLE II-continued

Recovery Necropsy (after 28-day recovery)

Group/Mean Lung Dose

| Organ | Lesion | Sex | Saline 0 mg/kg | Low 14-day 8.2 mg/kg | Low 28-day 11 mg/kg | High 14-day 16.5 mg/kg | Mid 28-day 21 mg/kg | High 28-day 31 mg/kg | Mixture 14-day 11.5 mg/kg | Mixture 28 day 34 mg/kg |
|---|---|---|---|---|---|---|---|---|---|---|
| | | | | | Incidence (group mean severity score) | | | | | |
| | Diffuse macrophage accumulation | M | 0/5 (0.00) | 0/5 | 0/5 (0.00) | 0/5 | 0/5 (0.00) | 0/5 (0.00) | 0/5 | 0/5 (0.00) |
| | Diffuse macrophage accumulation | F | 0/5 (0.00) | 0/5 | 0/5 (0.00) | 0/5 | 0/5 (0.00) | 0/5 (0.00) | 0/5 | 0/5 (0.00) |
| | Monocyte interstitial infiltration, alveolar wall | M | 0/5 (0.00) | 1/5 (0.20) | 0/5 (0.00) | 0/5 | 4/5 (1.00) | 5/5 (1.20) | 0/5 | 1/5 (0.20) |
| | Monocyte interstitial infiltration, alveolar wall | F | 0/5 (0.00) | 2/5 (0.40) | 4/5 (1.00) | 3/5 (0.60) | 5/5 (1.20) | 5/5 (1.40) | 0/5 | 4/5 (0.80) |
| Larynx | Squamous cell hyperplasia-metaplasia | M | 0/5 (0.00) | | 0/5 (0.00) | | 0/5 (0.00) | 0/5 (0.00) | | 0/5 (0.00) |
| | Squamous cell hyperplasia-metaplasia | F | 0/4 (0.00) | | 0/5 (0.00) | | 0/5 (0.00) | 0/5 (0.00) | | 0/5 (0.00) |

TABLE III

Recovery Necropsy (after 56-day recovery)

Group/Mean Lung Dose (Human Dose)

| Organ | Lesion | Sex | Saline 0 mg/kg | Low 11 mg/kg | Mid 21 mg/kg | High 31 mg/kg | Mixture 34 mg/kg |
|---|---|---|---|---|---|---|---|
| | | | Incidence (group mean severity score) | | | | |
| Lung | Focal macrophage accumulation | M | 0/6 (0.00)* | 1/5 (0.20) | 6/6 (2.33) | 6/6 (2.00) | 0/6 (0.00) |
| | Focal macrophage accumulation | F | 1/6 (0.17) | 4/5 (1.40) | 6/6 (2.33) | 6/6 (2.83) | 1/6 (0.17) |
| | Diffuse macrophage accumulation | M | 0/6 (0.00) | 0/5 (0.00) | 0/6 (0.00) | 0/6 (0.00) | 0/6 (0.00) |
| | Diffuse macrophage accumulation | F | 0/6 (0.00) | 0/5 (0.00) | 0/6 (0.00) | 0/6 (0.00) | 0/6.(0.00) |
| | Monocyte interstitial infiltration, alveolar wall | M | 0/6 (0.00) | 0/5 (0.00) | 6/6 (1.50) | 5/6 (1.17) | 0/6 (0.00) |
| | Monocyte interstitial infiltration, alveolar wall | F | 0/6 (0.00) | 2/5 (0.60) | 6/6 (1.50) | 6/6 (1.67) | 0/6 (0.00) |
| | Fibrosis, alveolar wall | M | 0/6 (0.00) | 0/5 (0.00) | 5/6 (0.83) | 4/6 (0.67) | 0/6 (0.00) |
| | Fibrosis, alveolar wall | F | 0/6 (0.00) | 2/5 (0.40) | 5/6 (0.83) | 5/6 (0.83) | 0/6 (0.00) |
| | Crystals, alveolar lumen | M | 0/6 (0.00) | 0/5 (0.00) | 4/6 (1.17) | 5/6 (1.17) | 0/6 (0.00) |
| | Crystals, alveolar lumen | F | 0/6 (0.00) | 2/5 (0.40) | 5/6 (1.33) | 5/6 (1.33) | 0/6 (0.00) |
| Larynx | Squamous cell hyperplasia-metaplasia | M | 0/6 (0.00) | 0/5 (0.00) | 0/6 (0.00) | 0/6 (0.00) | 0/6 (0.00) |
| | Squamous cell hyperplasia-metaplasia | F | 0/6 (0.00) | 0/5 (0.00) | 0/6 (0.00) | 0/6 (0.00) | 0/6 (0.00) |

In contrast, a fourth group of rats exposed to a combination of encapsulated and free ciprofloxacin for a similar treatment duration experienced a reduction in histopathology findings (Table II). After the 56 day recovery period, the histopathology findings for this group of rats was not significantly different from controls (Table III).

Figure 3:
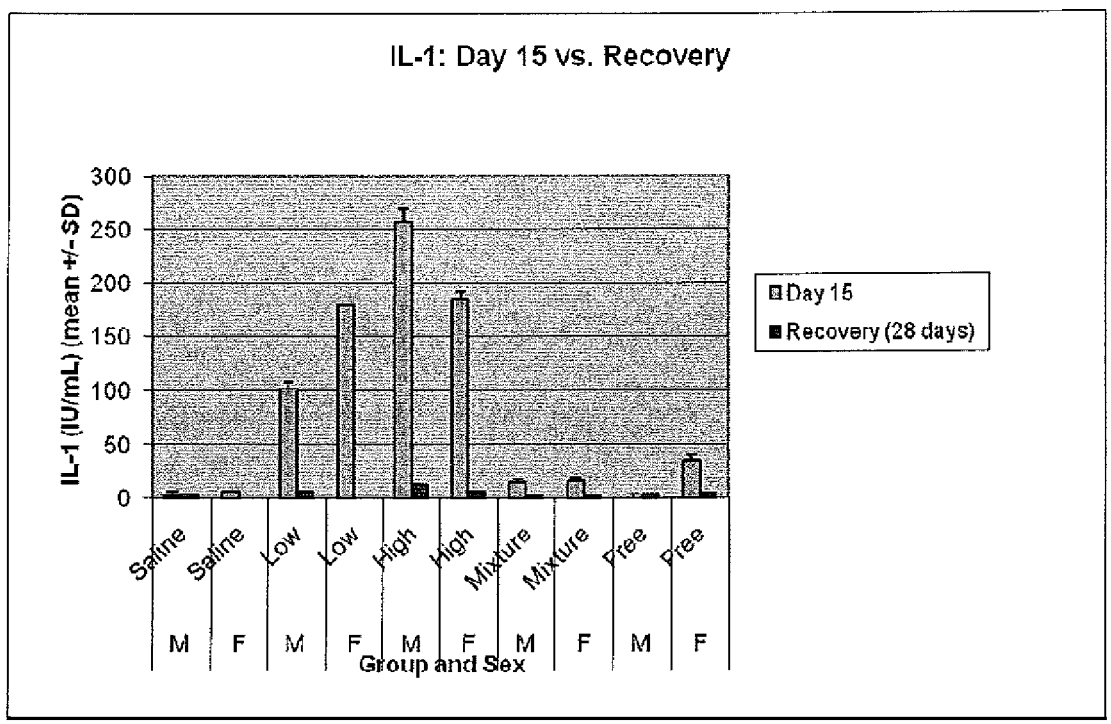
FIG. 3 is a bar graph showing increases in levels of IL-1 following 14 days of inhalation of either control (Saline), low dose liposomal ciprofloxacin (Low), high dose liposomal ciprofloxacin (High), combination of free and liposomal ciprofloxacin (Mixture) and free ciprofloxacin (Free). The dark bars on the graph show the levels all return to baseline values after the 28 day recovery evaluation.

The explanation for this surprising effect may be that the presence of free ciprofloxacin in the lung attenuates the release of cytokines which attract macrophages into the lung. The concentration of one cytokine marker, IL-1, in the lungs of rats after 14 days of inhalation treatment increases with increasing doses of liposomal ciprofloxacin (FIG. 3). The addition of free ciprofloxacin to the liposomal ciprofloxacin formulation reduces the levels of IL-1 to values similar to those for the control animals. These findings suggest that the presence of free ciprofloxacin down regulates cytokine markers and reduces the influx of macrophages into the lungs.

The instant invention is shown and described herein in a manner which is considered to be the most practical and preferred embodiments. It is recognized, however, that departures may be made therefrom which are within the scope of the invention and that obvious modifications will occur to one skilled in the art upon reading this disclosure.

While the instant invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

Each of the following is incorporated by reference.

Abbey D E, Hwang B L, Burchette R J, Vancuren T, Milss P K. Estimated Long-Term Ambient Concentrations of PM10 and Development of Respiratory Symptoms in Nonsmoking Population. Arch Environ Health 1995; 50(2): 139-151.

Almeida J A, Runge S, Mülleret R H, Peptide-loaded solid lipid nanoparticles (SLN): Influence of production parameters. Int J Pharm. 149 (2) (1997) 255-265.

Bangham A D, Standish M M, Watkins J C, Diffusion of univalent ions across the lamellae of swollen phospholipids. J Mol Biol. 13 (1) (1965) 238-252.

Choudhury A, Gordian M E, Morris S. Associations Between Respiratory Illness and PM10 Air Pollution. Arch Environ health 1997; 54(2): 113-117.

Conforti A, Franco L, Milamino R, Velo G P, Boccu E, Largajolli E, Schiavon O, Veronese F M. PEG superoxide dismutase derivatives: anti-inflammatory activity in carrageenan pleurisy in rats. Pharm Research Commun. 19, pg. 287, 1987.

Costerton J W, Lewandowski Z, Caldwell D E, Korber D R, Lappin-Scott H M., Microbial biofilms. Annu Rev Microbiol. 1995; 49:711-45.

Fitzsimmons S C. The changing epidemiology of cystic fibrosis. J Pediatr. 1993 January; 122(1):1-9.

Gilbert P, Das J, Foley I., Biofilm susceptibility to antimicrobials. Adv Dent Res. 1997 April; 11(1):160-7.

Helle J, Barr J, Ng S Y, Shen H R, Schwach-Abdellaoui K, Gurny R, Vivien-Castioni N, Loup P J, Baehni P, Mombelli A. Development and applications of injectable poly(ortho esters) for pain control and periodontal treatment. Biomaterials, 23, 2002, 4397-4404.

Hodson M, Shah P L, DNase trials in cystic fibrosis. Respiration 1995; 62, Suppl 1: 29-32.

Katre N V, Knauf M J, Laird W J., Chemical modification of recombinant interleukin 2 by polyethylene glycol increases its potency in the murine Meth A sarcoma model. Proc Natl Acad. Sci. U.S.A. vol. 84, 1487-91, 1987.

Koren H. Association between Criteria Air Pollutants and Asthma. Environ Health Perpec 1995; 103(6): 235-242.

LiPuma J J., Microbiological and immunologic considerations with aerosolized drug delivery. Chest. 2001 September; 120(3 Suppl):118S-123S.

Lode H, Borner K, Koeppe P, Schaberg T., Azithromycin—review of key chemical, pharmacokinetic and microbiological features. J Antimicrob Chemother. 1996; 37, Suppl C: 1-8

Moss R B., Administration of aerosolized antibiotics in cystic fibrosis patients. Chest. 2001 September; 120(3 Suppl):107S-113S.

Niven R N and Schreier H. Nebulization of Liposomes: I. Effects of Lipid Composition. Pharm Res. 1990; 7:1127-1133.

Nurkiewicz T R, Porter D W, Barger M, Castranova V, Boegehold M A: Particulate matter exposure impairs systemic microvascular endothelium-dependent dilation. Environ Health Perspect 2004, 112:1299-1306

Nurkiewicz T R, Porter D W, Hubbs A F, Cumpston J L, Chen B T, Frazer D G, Castranova V., Nanoparticle inhalation augments particle-dependent systemic microvascular dysfunction. Particle and Fibre Tox., 2008. 5:1.

Passirani C, Barratt G, Devissaguet J P, Labarre D., Long-circulating nanoparticles bearing heparin or dextran covalently bound to poly(methyl methacrylate). Pharm Res. 1998 July; 15(7):1046-50.

Peppas Bures P, Leobandung W, Ichikawa H., Hydrogels in pharmaceutical formulations. Eur J of Pharm and Biopharm. 2000 July; 50(1):27-46. Review.

Polonio R E Mermel L A, Paquette G E, Sperry J F., Eradication of biofilm-forming Staphylococcus epidermidis (RP62A) by a combination of sodium salicylate and vancomycin. Antimicrob Agents Chemother. 2001 November; 45(11):3262-6.

Pope C A, Bates D, Raizenne M. Health Effects of Particulate Air Pollution: Time for Reassessment? Environ Health Perspec 1995; 103: 472-480.

Schroeder S A Gaughan D M, Swift M., Protection against bronchial asthma by CFTR delta F508 mutation: a heterozygote advantage in cystic fibrosis. Nat. Med. 1995 July; 1(7): 703-5.

Sciarra J J, Patel S P., In vitro release of therapeutically active ingredients from polymer matrixes. J of Pharm Sci. 1976 October; 65(10):1519-22.

Smith A L, Ramsey B W, Hedges D L, Hack B, Williams-Warren J, Weber A, Gore E J, Redding G J. Safety of aerosol tobramycin administration for 3 months to patients with cystic fibrosis. Ped Pulmonol. 1989; 7(4):265-271.

Thorgeirsdottir T O, Kjoniksen A L, Knudsen K D, Kristmundsdottir T, Nystrom B. Viscoelastic and Structural Properties of Pharmaceutical Hydrogels Containing Monocaprin. Eur. J. of Pharm. and Biopharm. 2005 February; 59(2):333-42.

Van Heeckeren A M, Schluchter M D, Drumm M L, Davis P B. Role of Cftr genotype in the response to chronic Pseudomonas aeruginosa lung infection in mice. Am J Physiol Lung Cell Mol Physiol. 2004 November; 287(5): L944-52. Epub 2004 Jul. 9.

Van Heeckeren A M, Scaria A, Schluchter M D, Ferkol T W, Wadsworth S, Davis P B. Delivery of CFTR by adenoviral vector to cystic fibrosis mouse lung in a model of chronic

*Pseudomonas aeruginosa* lung infection. Am J Physiol Lung Cell Mol Physiol. 2004 April; 286(4)1717-26. Epub 2003 Sep. 26.

Van Heeckeren A, Ferkol T, Tosi M., Effects of bronchopulmonary inflammation induced by *pseudomonas aeruginosa* on adenovirus-mediated gene transfer to airway epithelial cells in mice. Gene Ther. 1998 March; 5(3):345-51.

Van Heeckeren A M, Schluchter M D., Murine models of chronic *Pseudomonas aeruginosa* lung infection. Lab Anim. 2002 July; 36(3):291-312.

Van Heeckeren A M, Tscheikuna J, Walenga R W, Konstan M W, Davis P B, Erokwu B, Haxhiu M A, Ferkol T W. Effect of *Pseudomonas* infection on weight loss, lung mechanics, and cytokines in mice. Am J Respir Crit Care Med. 2000 January; 161(1):271-9.

Weber A, Smith A, Williams-Warren J, Ramsey B, Covert D S., Nebulizer delivery of tobramycin to the lower respiratory tract. Pediatr Pulmonol. 1994 May; 17(5):331-9.

Wolter J, Seeney S, Bell S, Bowler S, Masel P, McCormack J., Effect of long term treatment with azithromycin on disease parameters in cystic fibrosis: a randomised trial. Thorax 2002; 57: 212-216.

Woodle M C, Storm G, Newman M S, Jekot J J, Collins L R, Martin F J, Szoka F C Jr., Prolonged systemic delivery of peptide drugs by long-circulating liposomes: illustration with vasopressin in the Brattleboro rat. Pharm Res. 1992 February; 9(2):260-5.

Zielenski J, Tsui L C., Cystic fibrosis: genotypic and phenotypic variations. Annual Rev Genet. 1995; 29:777-807.

Ye, Q, Asherman J, Stevenson M, Brownson E, Katre N V., DepoFoam technology: a vehicle for controlled delivery of protein and peptide drugs. J Control Rel. February 14; 64(1-3):155-66.

Yevich P P, Lung structure—relation to response to particulate. Arch. Environ. Health 10: 37-43 (1965).

What is claimed is:

1. An aerosolized composition of particles, comprising:
  a free, unencapsulated ciprofloxacin in an aqueous solution with sodium acetate at a pH of 3.2; and
  a liposome-encapsulated ciprofloxacin;
  wherein the composition is formulated for aerosolized delivery to a human lung and particles of the aerosol have a diameter in a range from about 2 microns to about 4 microns; and
  wherein the free, unencapsulated ciprofloxacin is in the aqueous solution at a concentration of about 30 mg/mL.

* * * * *